United States Patent
Tajima

(10) Patent No.: US 10,634,799 B2
(45) Date of Patent: Apr. 28, 2020

(54) RADIOGRAPHY SYSTEM, RADIOGRAPHY METHOD, AND RADIOGRAPHY PROGRAM STORAGE MEDIUM

(71) Applicant: FUJIFILM CORPORATION, Minato-ku, Tokyo (JP)

(72) Inventor: Takashi Tajima, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 298 days.

(21) Appl. No.: 15/660,954

(22) Filed: Jul. 27, 2017

(65) Prior Publication Data

US 2018/0031714 A1   Feb. 1, 2018

(30) Foreign Application Priority Data

Jul. 29, 2016   (JP) .................................. 2016-150588
Jul. 24, 2017   (JP) .................................. 2017-142640

(51) Int. Cl.

| | | |
|---|---|---|
| *G01T 1/20* | (2006.01) | |
| *G01T 1/208* | (2006.01) | |
| *G01T 1/29* | (2006.01) | |
| *H04N 5/225* | (2006.01) | |
| *A61B 6/00* | (2006.01) | |

(Continued)

(52) U.S. Cl.
CPC ............ *G01T 1/208* (2013.01); *A61B 6/4233* (2013.01); *A61B 6/4266* (2013.01); *A61B 6/505* (2013.01); *G01T 1/17* (2013.01); *G01T 1/2023* (2013.01); *G01T 1/2928* (2013.01); *H04N 5/2251* (2013.01); *H04N 5/32* (2013.01)

(58) Field of Classification Search
CPC ...... G01T 1/208; A61B 6/4233; A61B 6/4266
See application file for complete search history.

(56) References Cited

U.S. PATENT DOCUMENTS

| | | | |
|---|---|---|---|
| 6,380,542 B1 | 4/2002 | Shimura | |
| 2014/0161228 A1* | 6/2014 | Kitano | A61B 6/542 |
| | | | 378/62 |

FOREIGN PATENT DOCUMENTS

| | | | |
|---|---|---|---|
| JP | 2000-137099 A | 5/2000 | |
| JP | 2004-283410 A | 10/2004 | |

(Continued)

OTHER PUBLICATIONS

English language translation of the following: Office action dated May 21, 2019 from the JPO in a Japanese patent application No. 2017-142640 corresponding to the instant patent application.

*Primary Examiner* — Hugh Maupin
(74) *Attorney, Agent, or Firm* — SOLARIS Intellectual Property Group, PLLC

(57) ABSTRACT

A radiography system includes a radiography apparatus including first and second radiation detectors and, in a case in which a value corresponding to at least one of a first electric signal or a second electric signal is less than a threshold value, a console derives second imaging conditions using at least one of the first electric signal or the second electric signal, the first electric signal being a signal obtained by converting charge generated in the pixels of the first radiation detector under first imaging conditions, and having a level that increases as an amount of charge increases, the second electric signal being a signal obtained by converting charge generated in the pixels of the second radiation detector under the first imaging conditions, and having a level that increases as an amount of charge increases.

15 Claims, 21 Drawing Sheets

(51) Int. Cl.
    *G01T 1/202*     (2006.01)
    *H04N 5/32*     (2006.01)
    *G01T 1/17*     (2006.01)

(56) References Cited

FOREIGN PATENT DOCUMENTS

| | | |
|---|---|---|
| JP | 4177892 B2 | 11/2008 |
| JP | 2011-000235 A | 1/2011 |
| JP | 2015-019789 A | 2/2015 |
| WO | 9635372 A2 | 11/1996 |

\* cited by examiner

RADIOGRAPHY SYSTEM, RADIOGRAPHY METHOD, AND RADIOGRAPHY PROGRAM STORAGE MEDIUM

CROSS-REFERENCE TO RELATED APPLICATIONS

This application claims priority from Japanese Patent Applications Nos. 2016-150588, filed on Jul. 29, 2016, and 2017-142640, filed on Jul. 24, 2017, the disclosures of which are incorporated by reference herein in their entirety.

BACKGROUND

Field of the Invention

The present disclosure relates to a radiography system, a radiography method, and a radiography program.

Related Art

A radiography apparatus has been known which comprises two radiation detectors each of which includes a plurality of pixels accumulating charge corresponding to emitted radiation and which are provided so as to be stacked. In this type of radiography apparatus, a technique has been known which measures the bone density of a subject, using electric signals corresponding to the amounts of radiation emitted to each radiation detector (see JP4177892B).

In addition, a technique has been known which comprises one radiation detector, irradiates the radiation detector with two types of radiation with different energy levels in a time division manner, and measures the bone density of a subject from electric signals corresponding to the amounts of two kinds of radiation which are output from the radiation detector (see JP2015-019789A).

However, in a case in which radiographic images are captured by the radiography apparatus including two radiation detectors disclosed in, for example, JP4177892B under predetermined imaging conditions, a portion of the radiation emitted to a first radiation detector that is provided on the incident side of the radiation is absorbed by the first radiation detector. Therefore, in this case, the amount of radiation that reaches a second radiation detector, which is provided so as to be stacked on the side of the first radiation detector from which the radiation is transmitted and emitted, is less than the amount of radiation that reaches the first radiation detector.

In this case, the amount of radiation that reaches the second radiation detector is insufficient to capture a radiographic image and an appropriate radiographic image may not be captured according to imaging conditions. In this case, a user, such as a radiology technician, needs to determine new imaging conditions for appropriately capturing a radiographic image, which causes an increase in the workload of the user. The techniques disclosed in JP4177892B and JP2015-019789A do not consider the problems.

SUMMARY

The present disclosure has been made in view of the above-mentioned problems and an object of the present disclosure is to reduce the workload of a user.

In order to achieve the object, according to an aspect of the present disclosure, there is provided a radiography system including: a radiography apparatus including a first radiation detector in which a plurality of pixels, each of which includes a conversion element that generates a larger amount of charge as it is irradiated with a larger amount of radiation, are two-dimensionally arranged and a second radiation detector which is provided so as to be stacked on a side of the first radiation detector from which the radiation is transmitted and emitted and in which a plurality of pixels, each of which includes a conversion element that generates a larger amount of charge as it is irradiated with a larger amount of radiation, are two-dimensionally arranged; and a derivation unit that is configured to, in a case in which a value corresponding to at least one of a first electric signal or a second electric signal is less than a threshold value, derive second imaging conditions using at least one of the first electric signal or the second electric signal, the first electric signal being a signal obtained by converting charge generated in the pixels of the first radiation detector when imaging is performed by the radiography apparatus under first imaging conditions, and having a level that increases as an amount of charge increases, the second electric signal being a signal obtained by converting charge generated in the pixels of the second radiation detector in when imaging is performed by the radiography apparatus under the first imaging conditions, and having a level that increases as an amount of charge increases.

In the radiography system according to the aspect of the present disclosure, the first imaging conditions may include a number of imaging operations, a tube voltage and an amount of radiation including a tube current, which are set to a radiation source that emits the radiation, and the derivation unit may be further configured to, in a case in which an amount of charge accumulated in the pixels of the second radiation detector when imaging is performed by the radiography apparatus under the first imaging conditions is less than the threshold value, derive, as the second imaging conditions, the tube voltage and the amount of radiation including the tube current at which the amount of charge is equal to or greater than the threshold value in a case in which a number of imaging operations is equal to the number of imaging operations in the first imaging conditions.

In the radiography system according to the aspect of the present disclosure may further include a detection unit that is configured to detect an amount of radiation emitted to the second radiation detector, the first imaging conditions may include a number of imaging operations, a tube voltage and an amount of radiation including a tube current, which are set to a radiation source that emits the radiation, and the derivation unit may be further configured to, in a case in which an accumulation value of the amount of radiation detected by the detection unit when imaging is performed by the radiography apparatus under the first imaging conditions is less than the threshold value, derive, as the second imaging conditions, the tube voltage and the amount of radiation including the tube current at which the accumulation value is equal to or greater than the threshold value in a case in which a number of imaging operations is equal to the number of imaging operations in the first imaging conditions.

In the radiography system according to the aspect of the present disclosure, the first imaging conditions may include a tube voltage and an amount of radiation including a tube current, which are set to a radiation source that emits the radiation in a preliminary imaging operation that is performed prior to a main imaging operation and in which an amount of radiation is less than an amount of radiation in the main imaging operation, and the derivation unit may be further configured to, in a case in which the amount of charge accumulated in the pixels of the first radiation detector when imaging is performed by the radiography apparatus under the first imaging conditions is less than the threshold value, derive, as the second imaging conditions, the tube voltage and the amount of radiation including the tube current, at which the amount of charge accumulated in the pixels of the second radiation detector in the main imaging operation is equal to or greater than the threshold value in the main imaging operation, using the amount of charge accumulated in the pixels of the first radiation detector and a predetermined radiation transmittance of the first radiation detector.

In the radiography system according to the aspect of the present disclosure, the derivation unit may be configured to derive, as the second imaging conditions, the tube current at which the amount of charge accumulated in the pixels of the second radiation detector is equal to or greater than the threshold value in a case in which the tube voltage is equal to the tube voltage in the first imaging conditions, and the derivation unit may be configured to, in a case in which the derived tube current is greater than an upper limit that can be set to the radiation source, set the tube current in the second imaging conditions to an upper limit and derive, as the tube voltage in the second imaging conditions, a tube voltage at which the amount of charge is equal to or greater than the threshold value.

In the radiography system according to the aspect of the present disclosure, the first imaging conditions may include a number of imaging operations, a tube voltage and an amount of radiation including a tube current, which are set to a radiation source that emits the radiation, and the derivation unit may be configured to, in a case in which an amount of charge accumulated in the pixels of the second radiation detector when imaging is performed by the radiography apparatus under the first imaging conditions is less than the threshold value, derive, as the second imaging conditions, imaging conditions in which the tube voltage and the amount of radiation including the tube current is equal to the tube voltage and the amount of radiation including the tube current in the first imaging conditions, and the number of imaging operations is larger than the number of imaging operations in the first imaging conditions.

The radiography system according to the aspect of the present disclosure may further comprise an execution unit that is configured to perform radiographic imaging under the second imaging conditions derived by the derivation unit.

The radiography system according to the aspect of the present disclosure may further comprise a display unit that is configured to display the second imaging conditions derived by the derivation unit.

In the radiography system according to the aspect of the present disclosure, the derivation unit may be further configured to derive an estimated value of the amount of radiation emitted to the first radiation detector in a case in which the radiation is emitted with the tube voltage and the amount of radiation including the tube current derived as the second imaging conditions, and the derivation unit may be further configured to, in a case in which the derived estimated value is greater than an upper limit, derive, as the second imaging conditions, the number of imaging operations that is larger than the number of imaging operations in the first imaging conditions again.

Particularly, in the radiography system according to the aspect of the present disclosure, the derivation unit may be configured to derive a tube voltage that is higher than the tube voltage in a first imaging operation as the tube voltage in the second and subsequent imaging operations in the second imaging conditions.

In the radiography system according to the aspect of the present disclosure, each of the first radiation detector and the second radiation detector may include a light emitting layer that is irradiated with radiation and emits light, the plurality of pixels of each of the first radiation detector and the second radiation detector may generate and accumulate the charge as a result of receiving the light, and the light emitting layer of the first radiation detector and the light emitting layer of the second radiation detector may have different compositions.

In the radiography system according to the aspect of the present disclosure, the light emitting layer of the first radiation detector may include CsI and the light emitting layer of the second radiation detector may include GOS.

In the radiography system according to the aspect of the present disclosure, the derivation unit may be configured to derive at least one of bone mineral content or bone density, using a first radiographic image captured by the first radiation detector and a second radiographic image captured by the second radiation detector according to the second imaging conditions.

In order to achieve the object, according to another aspect of the present disclosure, there is provided a radiography method that is performed by a radiography apparatus comprising a first radiation detector in which a plurality of pixels, each of which includes a conversion element that generates a larger amount of charge as it is irradiated with a larger amount of radiation, are two-dimensionally arranged and a second radiation detector which is provided so as to be stacked on a side of the first radiation detector from which the radiation is transmitted and emitted and in which a plurality of pixels, each of which includes a conversion element that generates a larger amount of charge as it is irradiated with a larger amount of radiation, are two-dimensionally arranged. The radiography method may include: in a case in which a value corresponding to at least one of a first electric signal or a second electric signal is less than a threshold value, deriving second imaging conditions using at least one of the first electric signal or the second electric signal, the first electric signal being a signal obtained by converting charge generated in the pixels of the first radiation detector when imaging is performed by the radiography apparatus under first imaging conditions, and having a level that increases as an amount of charge increases, the second electric signal being a signal obtained by converting charge generated in the pixels of the second radiation detector when imaging is performed by the radiography apparatus under the first imaging conditions, and having a level that increases as an amount of charge increases.

In order to achieve the object, according to still another aspect of the present disclosure, there is provided non-transitory storage medium storing a radiography program that causes a computer to execute a control processing of a radiography apparatus comprising a first radiation detector in which a plurality of pixels, each of which includes a conversion element that generates a larger amount of charge as it is irradiated with a larger amount of radiation, are two-dimensionally arranged and a second radiation detector which is provided so as to be stacked on a side of the first radiation detector from which the radiation is transmitted and emitted and in which a plurality of pixels, each of which includes a conversion element that generates a larger amount of charge as it is irradiated with a larger amount of radiation, are two-dimensionally arranged, the control processing including: in a case in which a value corresponding to at least one of a first electric signal or a second electric signal is less than a threshold value, deriving second imaging conditions using at least one of the first electric signal or the second electric signal, the first electric being a signal obtained by converting charge generated in the pixels of the first radiation detector when imaging is performed by the radiography apparatus under first imaging conditions, and having a level that increases as an amount of charge increases, and the second electric signal being a signal obtained by converting charge generated in the pixels of the second radiation detector when imaging is performed by the radiography apparatus under the first imaging conditions, and having a level that increases as an amount of charge increases.

According to the present disclosure, it is possible to reduce the workload of a user.

DETAILED DESCRIPTION

Hereinafter, embodiments of the invention will be described in detail with reference to the drawings.

First Embodiment

Figure 1:
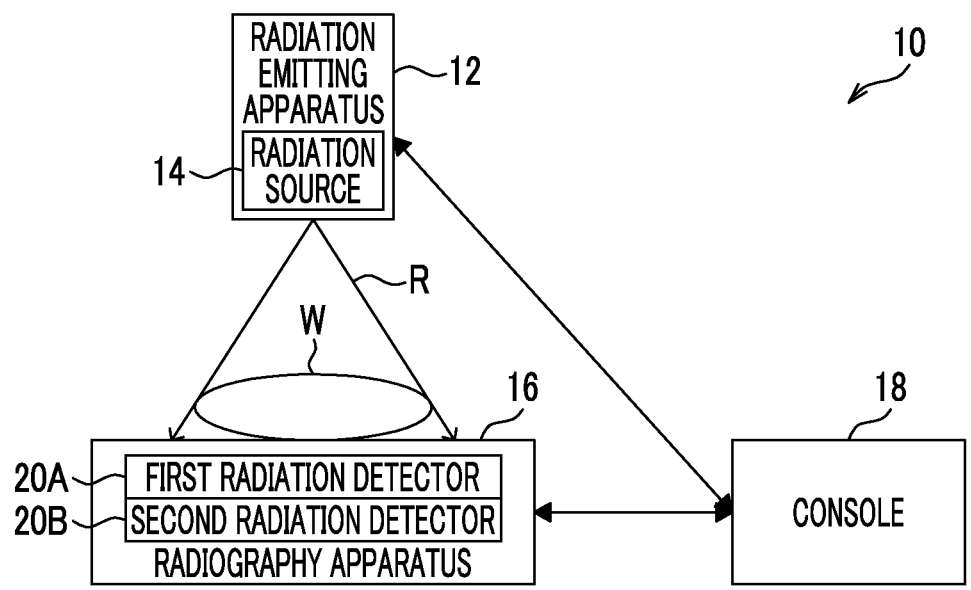
FIG. 1 is a block diagram illustrating an example of the structure of a radiography system according to each embodiment.

First, the structure of a radiography system 10 according to this embodiment will be described with reference to FIG. 1. As illustrated in FIG. 1, the radiography system 10 comprises a radiation emitting apparatus 12, a radiography apparatus 16, and a console 18.

The radiation emitting apparatus 12 according to this embodiment comprises a radiation source 14 that irradiates a subject W, which is an example of an imaging target, with radiation R such as X-rays. An example of the radiation emitting apparatus 12 is a treatment cart. A method for instructing the radiation emitting apparatus 12 to emit the radiation R is not particularly limited. For example, in a case in which the radiation emitting apparatus 12 comprises an irradiation button, a user, such as a radiology technician, may press the irradiation button to instruct the emission of the radiation R such that the radiation R is emitted from the radiation emitting apparatus 12. In addition, for example, the user, such as a radiology technician, may operate the console 18 to instruct the emission of the radiation R such that the radiation R is emitted from the radiation emitting apparatus 12.

When receiving a command to emit the radiation R, the radiation emitting apparatus 12 emits the radiation R from the radiation source 14 according to set emission conditions, such as a tube voltage, a tube current, and an irradiation period. Hereinafter, the dose of the radiation R is simply referred to as "the amount of radiation".

The radiography apparatus 16 according to this embodiment comprises a first radiation detector 20A and a second radiation detector 20B that detect the radiation R which has been emitted from the radiation emitting apparatus 12 and then transmitted through the subject W. The radiography apparatus 16 captures radiographic images of the subject W using the first radiation detector 20A and the second radiation detector 20B. Hereinafter, in a case in which the first radiation detector 20A and the second radiation detector 20B do not need to be distinguished from each other, they are generically referred to as "radiation detectors 20".

Figure 2:
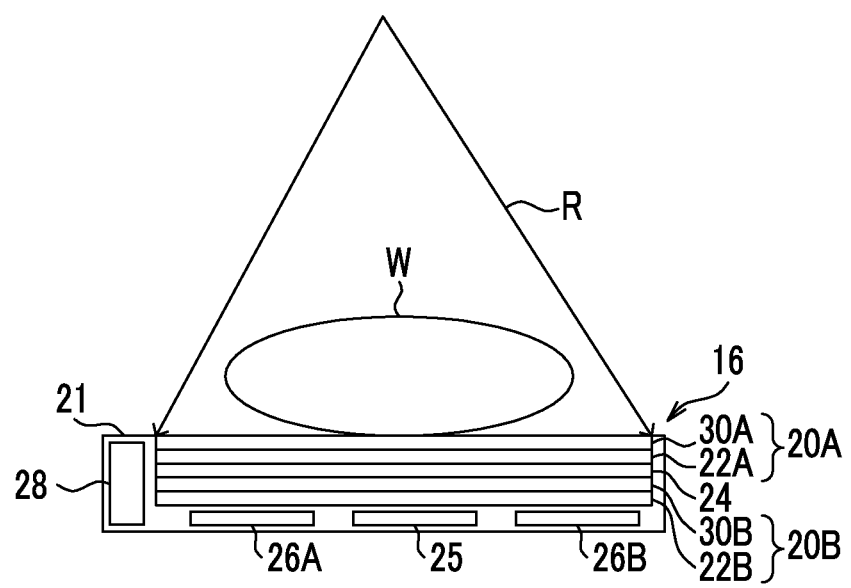
FIG. 2 is a side cross-sectional view illustrating an example of the structure of a radiography apparatus according to each embodiment.

Next, the structure of the radiography apparatus 16 according to this embodiment will be described with reference to FIG. 2. As illustrated in FIG. 2, the radiography apparatus 16 comprises a plate-shaped housing 21 that transmits the radiation R and has a waterproof, antibacterial, and airtight structure. The housing 21 includes the first radiation detector 20A, the second radiation detector 20B, a radiation limitation member 24, a control board 25, a control board 26A, a control board 26B, and a case 28.

The first radiation detector 20A is provided on the incident side of the radiation R and the second radiation detector 20B is provided so as to be stacked on the side of the first radiation detector 20A from which the radiation R is transmitted and emitted. The first radiation detector 20A comprises a thin film transistor (TFT) substrate 30A and a scintillator 22A which is an example of a light emitting layer that is irradiated with the radiation R and emits light. The TFT substrate 30A and the scintillator 22A are stacked in the order of the TFT substrate 30A and the scintillator 22A from the incident side of the radiation R. The term "stacked" means a state in which the first radiation detector 20A and the second radiation detector 20B overlap each other in a case in which the first radiation detector 20A and the second radiation detector 20B are seen from the incident side or the emission side of the radiation R in the radiography apparatus 16 and it does not matter how they overlap each other. For example, the first radiation detector 20A and the second radiation detector 20B, or the first radiation detector 20A, the radiation limitation member 24, and second radiation detector 20B may overlap while coming into contact with each other or may overlap with a gap therebetween in the stacking direction.

The second radiation detector 20B comprises a TFT substrate 30B and a scintillator 22B which is an example of the light emitting layer. The TFT substrate 30B and the scintillator 22B are stacked in the order of the TFT substrate 30B and the scintillator 22B from the incident side of the radiation R.

That is, the first radiation detector 20A and the second radiation detector 20B are so-called irradiation side sampling (ISS) radiation detectors that are irradiated with the radiation R from the side of the TFT substrates 30A and 30B.

In the radiography apparatus 16 according to this embodiment, the scintillator 22A of the first radiation detector 20A and the scintillator 22B of the second radiation detector 20B have different compositions. Specifically, for example, the scintillator 22A includes CsI (Tl) (cesium iodide having thallium added thereto) and the scintillator 22B includes gadolinium oxysulfide (GOS). In addition, a combination of the composition of the scintillator 22A and the composition of the scintillator 22B is not limited to the above-mentioned example and may be a combination of other compositions or a combination of the same compositions.

The radiation limitation member 24 that limits the transmission of the radiation R is provided between the first radiation detector 20A and the second radiation detector 20B. An example of the radiation limitation member 24 is a plate-shaped member made of, for example, copper and tin. It is preferable that the thickness of the plate-shaped member is uniform in the range in which the error of a variation in the thickness is equal to or less than 1%.

An electronic circuit, such as an integrated control unit 71 which will be described below, is formed on the control board 25. The control board 26A is provided so as to correspond to the first radiation detector 20A and electronic circuits, such as an image memory 56A and a control unit 58A which will be described below, are formed on the control board 26A. The control board 26B is provided so as to correspond to the second radiation detector 20B and electronic circuits, such as an image memory 56B and a control unit 58B which will be described below, are formed on the control board 26B. The control board 25, the control board 26A, and the control board 26B are provided on the side of the second radiation detector 20B which is opposite to the incident side of the radiation R.

The case 28 is provided at a position (that is, outside the range of an imaging region) that does not overlap the radiation detector 20 at one end of the housing 21. For example, a power supply unit 70 which will be described below is accommodated in the case 28. The installation position of the case 28 is not particularly limited. For example, the case 28 may be provided at a position that overlaps the radiation detector 20 on the side of the second radiation detector 20B which is opposite to the incident side of the radiation.

Next, the structure of a main portion of an electric system of the radiography apparatus 16 according to this embodiment will be described with reference to FIG. 3.

Figure 3:
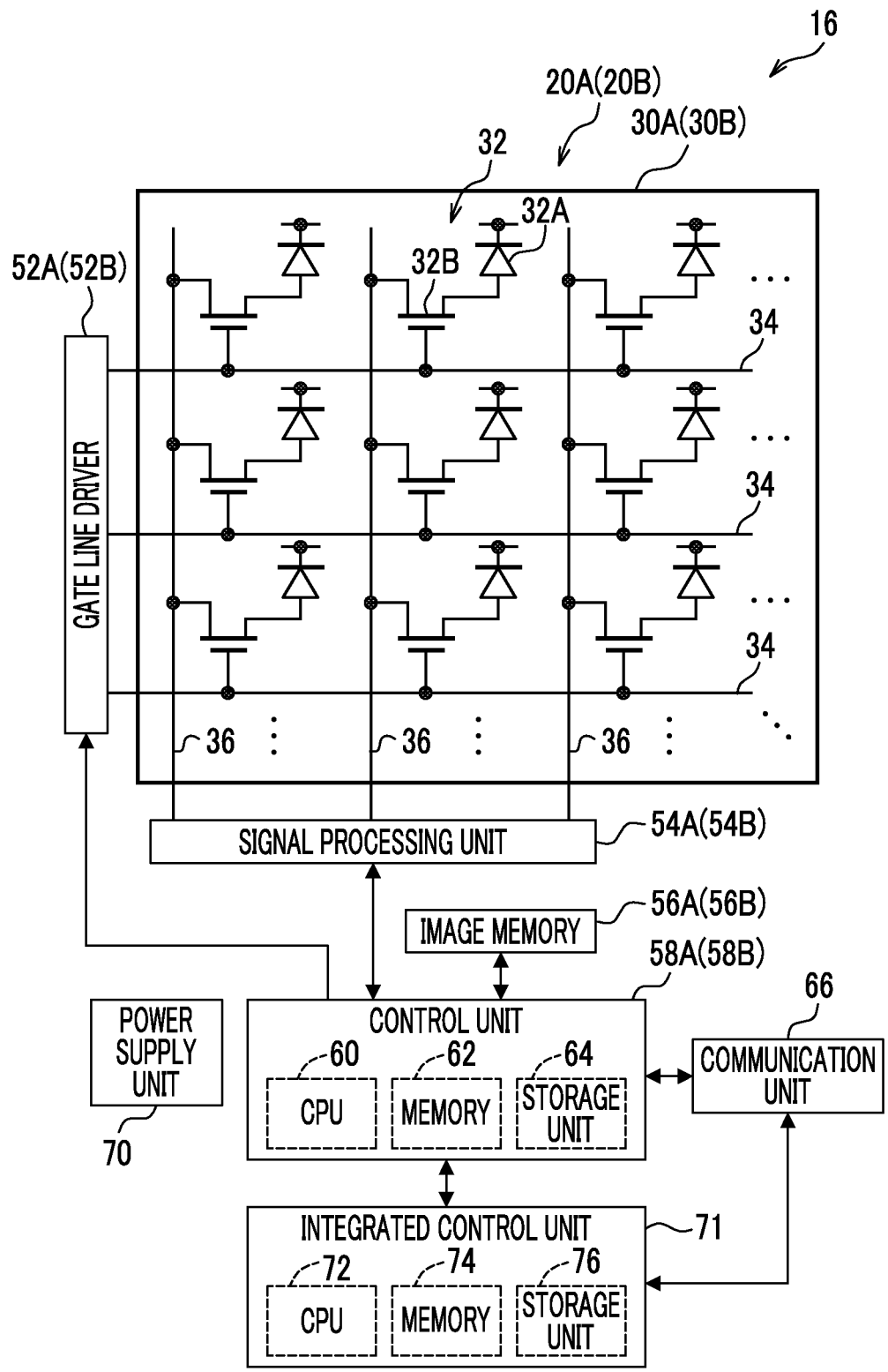
FIG. 3 is a block diagram illustrating an example of the structure of a main portion of an electric system of the radiography apparatus according to the first, third, and fourth embodiments.

As illustrated in FIG. 3, a plurality of pixels 32 are two-dimensionally provided in one direction (a row direction in FIG. 3) and an intersection direction (a column direction in FIG. 3) that intersects the one direction on the TFT substrate 30A. The pixel 32 includes a sensor unit 32A and a field effect thin film transistor (TFT; hereinafter, simply referred to as a "thin film transistor") 32B.

The sensor unit 32A includes, for example, an upper electrode, a lower electrode, and a photoelectric conversion film which are not illustrated, absorbs the light emitted from the scintillator 22A, generates charge, and accumulates the generated charge. The thin film transistor 32B converts the charge accumulated in the sensor unit 32A into an electric signal and outputs the electric signal. The sensor unit 32A is an example of a conversion element in which the amount of charge increases with an increase in the amount of radiation.

A plurality of gate lines 34 which extend in the one direction and are used to turn on and off each thin film transistor 32B are provided on the TFT substrate 30A. In addition, a plurality of data lines 36 which extend in the intersection direction and are used to read charge through the thin film transistors 32B in an on state are provided on the TFT substrate 30A.

A gate line driver 52A is provided on one side of two adjacent sides of the TFT substrate 30A and a signal processing unit 54A is provided on the other side. Each gate line 34 of the TFT substrate 30A is connected to the gate line driver 52A and each data line 36 of the TFT substrate 30A is connected to the signal processing unit 54A.

The rows of the thin film transistors 32C of the TFT substrate 30A are sequentially turned on by electric signals which are supplied from the gate line driver 52A through the gate lines 34. The charge which is read by the thin film transistor 32B in an on state is transmitted as an electric signal through the data line 36 and is input to the signal processing unit 54A. In this way, charge is sequentially read from each row of thin film transistors 32B and image data indicating a two-dimensional radiographic image is acquired.

The signal processing unit 54A comprises amplifying circuits (not illustrated) for amplifying an input electric signal and sample-and-hold circuits (not illustrated) which are provided for each data line 36. The electric signal transmitted through each data line 36 is amplified by the amplifying circuit and is then held by the sample-and-hold circuit. A multiplexer and an analog/digital (A/D) converter are connected to the output side of the sample-and-hold circuit in this order. The electric signals held by each sample-and-hold circuit are sequentially (serially) input to the multiplexer and are sequentially selected by the multiplexer. Then, the A/D converter converts the selected electric signals into digital image data.

The control unit 58A which will be described below is connected to the signal processing unit 54A. The image data output from the A/D converter of the signal processing unit 54A is sequentially output to the control unit 58A. The image memory 56A is connected to the control unit 58A. The image data sequentially output from the signal processing unit 54A is sequentially stored in the image memory 56A under the control of the control unit 58A. The image memory 56A has memory capacity that can store a predetermined amount of image data. Whenever a radiographic image is captured, captured image data is sequentially stored in the image memory 56A.

The control unit 58A comprises a central processing unit (CPU) 60, a memory 62 including, for example, a read only memory (ROM) and a random access memory (RAM), and a non-volatile storage unit 64 such as a flash memory. An example of the control unit 58A is a microcomputer.

The integrated control unit 71 comprises a CPU 72, a memory 74 including, for example, a ROM and a RAM, and a non-volatile storage unit 76 such as a flash memory. An example of the integrated control unit 71 is a microcomputer. The control unit 58A and the integrated control unit 71 are connected such that they can communicate with each other.

A communication unit 66 is connected to the control unit 58A and the integrated control unit 71 and transmits and receives various kinds of information to and from external apparatuses, such as the radiation emitting apparatus 12 and the console 18, using at least one of wireless communication or wired communication. The power supply unit 70 supplies power to each of the above-mentioned various circuits or elements (for example, the gate line driver 52A, the signal processing unit 54A, the image memory 56A, the control unit 58A, the integrated control unit 71, and the communication unit 66). In FIG. 3, lines for connecting the power supply unit 70 to various circuits and elements are not illustrated in order to avoid complication.

Components of the TFT substrate 30B, the gate line driver 52B, the signal processing unit 54B, the image memory 56B, and the control unit 58B of the second radiation detector 20B have the same structures as the corresponding components of the first radiation detector 20A and thus the description thereof will not be repeated here. The control unit 58A and the control unit 58B are connected such that they can communicate with each other.

According to the above-mentioned structure, the radiography apparatus 16 according to this embodiment captures radiographic images using the first radiation detector 20A and the second radiation detector 20B.

Figure 4:
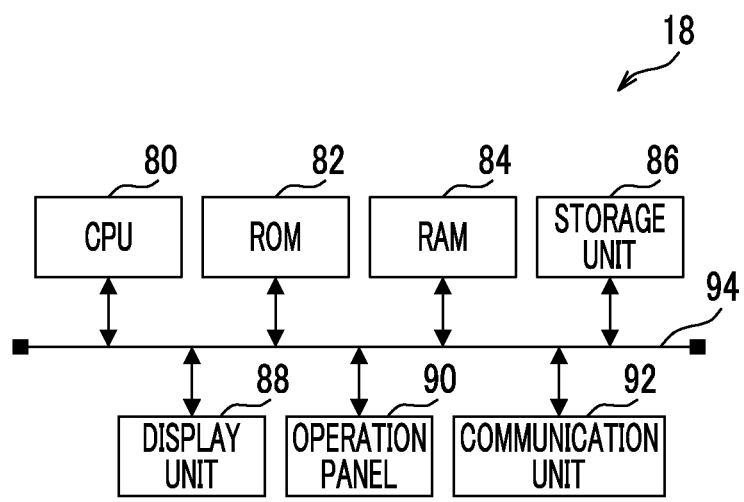
FIG. 4 is a block diagram illustrating an example of the structure of a main portion of an electric system of a console according to each embodiment.

Next, the structure of the console 18 according to this embodiment will be described with reference to FIG. 4. As illustrated in FIG. 4, the console 18 comprises a CPU 80 that controls the overall operation of the console 18 and a ROM 82 in which, for example, various programs or various parameters are stored in advance. In addition, the console 18 comprises a RAM 84 that is used as, for example, a work area when the CPU 80 executes various programs and a non-volatile storage unit 86 such as a hard disk drive (HDD).

The console 18 further comprises a display unit 88 that displays, for example, an operation menu and a captured radiographic image and an operation panel 90 which includes a plurality of keys and to which various kinds of information or operation commands are input. In addition, the console 18 comprises a communication unit 92 that transmits and receives various kinds of information to and from the external apparatuses, such as the radiation emitting apparatus 12 and the radiography apparatus 16, using at least one of wireless communication or wired communication. The CPU 80, the ROM 82, the RAM 84, the storage unit 86, the display unit 88, the operation panel 90, and the communication unit 92 are connected to each other through a bus 94.

In the radiography apparatus 16 according to this embodiment, since the first radiation detector 20A and the radiation limitation member 24 absorb the radiation R, the amount of radiation that reaches the second radiation detector 20B is less than the amount of radiation that reaches the first radiation detector 20A. In addition, the radiation limitation member 24 generally has the characteristic that it absorbs a larger number of low-energy components than high-energy components in energy forming the radiation R, which depends on the material forming the radiation limitation member 24. Therefore, the energy distribution of the radiation R that reaches the second radiation detector 20B has a larger number of high-energy components than the energy distribution of the radiation R that reaches the first radiation detector 20A.

In this embodiment, for example, about 50% of the radiation R that has reached the first radiation detector 20A is absorbed by the first radiation detector 20A and is used to capture a radiographic image. In addition, about 60% of the radiation R that has passed through the first radiation detector 20A and reached the radiation limitation member 24 is absorbed by the radiation limitation member 24. About 50% of the radiation R that has passed through the first radiation detector 20A and the radiation limitation member 24 and reached the second radiation detector 20B is absorbed by the second radiation detector 20B and is used to capture a radiographic image. Since the absorptance of the radiation by the radiation detector 20 and the radiation limitation member 24 varies depending on the energy of the radiation R, the shape of a spectrum changes.

That is, the amount of radiation the level of the electric signal generated by the second radiation detector 20B) used to capture a radiographic image by the second radiation detector 20B is about 20% of the amount of radiation used to capture a radiographic image by the first radiation detector 20A. In addition, the ratio of the amount of radiation used to capture a radiographic image by the second radiation detector 20B to the amount of radiation used to capture a radiographic image by the first radiation detector 20A is not limited to the above-mentioned ratio. However, it is preferable that the amount of radiation used to capture a radiographic image by the second radiation detector 20B is equal to or greater than 10% of the amount of radiation used to capture a radiographic image by the first radiation detector 20A in terms of diagnosis.

Figure 5:
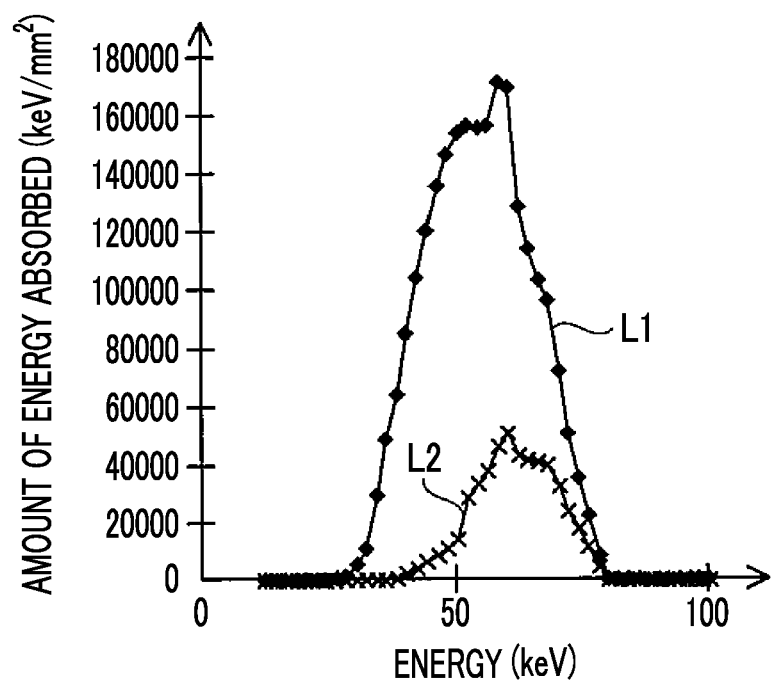
FIG. 5 is a graph illustrating the amount of radiation that reaches each of a first radiation detector and a second radiation detector according to each embodiment.

The radiation R is absorbed from a low-energy component. Therefore, for example, as illustrated in FIG. 5, the energy components of the radiation R that reaches the second radiation detector 20B do not include the low-energy components among the energy components of the radiation R that reaches the first radiation detector 20A. In FIG. 5, the vertical axis indicates the amount of radiation R absorbed per unit area and the horizontal axis indicates the energy of the radiation R in a case in which the tube voltage of the radiation source 14 is 80 kV. In addition, in FIG. 5, a solid line L1 indicates the relationship between the energy of the radiation R absorbed by the first radiation detector 20A and the amount of radiation R absorbed per unit area. In FIG. 5, a solid line L2 indicates the relationship between the energy of the radiation R absorbed by the second radiation detector 20B and the amount of radiation R absorbed per unit area.

As described above, the amount of radiation that reaches the second radiation detector 20B is less than the amount of radiation that reaches the first radiation detector 20A. Therefore, in a case in which a radiographic image is captured under predetermined first imaging conditions, the amount of radiation that reaches the second radiation detector 20B is likely to be insufficient to capture the radiographic image. Here, the imaging conditions include the exposure conditions, such as a tube voltage, a tube current, and an irradiation period set to the radiation emitting apparatus 12, and the number of imaging operations. Here, the number of imaging operations indicates the number of imaging operations in a series of imaging operations for obtaining an energy subtraction image and bone density which will be described below. In this embodiment, a case in which the number of imaging operations in the first imaging conditions is one will be described.

Specifically, for example, the number of imaging operations is one in a case in which one operation of starting the emission of the radiation R and one operation of stopping the emission of the radiation R are performed, each radiographic image is captured by each radiation detector 20, and an energy subtraction image and bone density are obtained from each radiographic image. In addition, for example, the number of imaging operations is two in a case in which two operations of starting the emission of the radiation R and two operations of stopping the emission of the radiation R are repeated, radiographic images are obtained by the first radiation detector 20A in each operation, and an energy subtraction image and bone density are obtained from each radiographic image.

In the capture of radiographic images under the first imaging conditions, in a case in which the amount of radiation that reaches the second radiation detector 20B is insufficient to capture a radiographic image, it is necessary to change the imaging conditions to second imaging conditions different from the first imaging conditions and to capture radiographic images again. Therefore, in a case in which a value that corresponds to at least one of a first electric signal or a second electric signal when the radiography apparatus 16 performs imaging under the first imaging conditions is less than a threshold value, the radiography apparatus 16 according to this embodiment derives the second imaging conditions, using at least one of the first electric signal or the second electric signal.

The first electric signal is an electric signal which is obtained by converting the charge generated in the pixel 32 of the first radiation detector 20A in a case in which the radiography apparatus 16 performs imaging under the first imaging conditions and of which the level increases as the amount of charge increases. The second electric signal is an electric signal which is obtained by converting the charge generated in the pixel 32 of the second radiation detector 20B in a case in which the radiography apparatus 16 performs imaging under the first imaging conditions and of which the level increases as the amount of charge increases.

In this embodiment, a case in which the charge accumulated in the pixel 32 of the first radiation detector 20A, specifically, the pixel value of the pixel 32 of the first radiation detector 20A is applied as the first electric signal will be described. In addition, a case in which the charge accumulated in the pixel 32 of the second radiation detector 20B, specifically, the pixel value of the pixel 32 of the second radiation detector 20B is applied as the second electric signal will be described.

Figure 6:
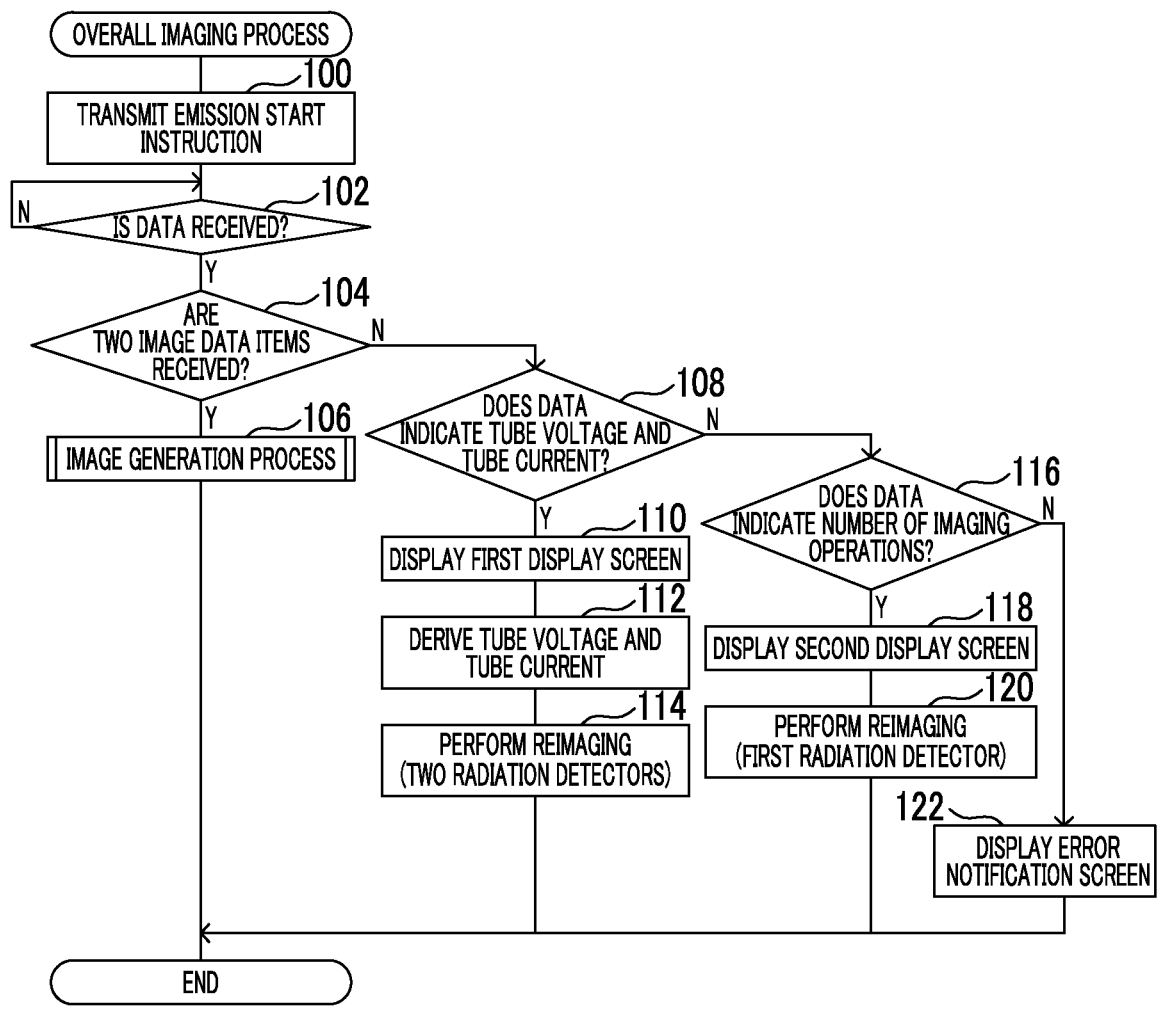
FIG. 6 is a flowchart illustrating the process flow of an overall imaging processing program according to the first and second embodiments.

Next, the operation of the radiography system 10 according to this embodiment will be described with reference to FIGS. 6 to 14. FIG. 6 is a flowchart illustrating the process flow of an overall imaging processing program which is executed by the CPU 80 of the console 18 in a case in which the user inputs an imaging menu including, for example, the name of the subject W, an imaging part, and the first imaging conditions through the operation panel 90. The overall imaging processing program is installed in the ROM 82 of the console 18 in advance.

Figure 12:
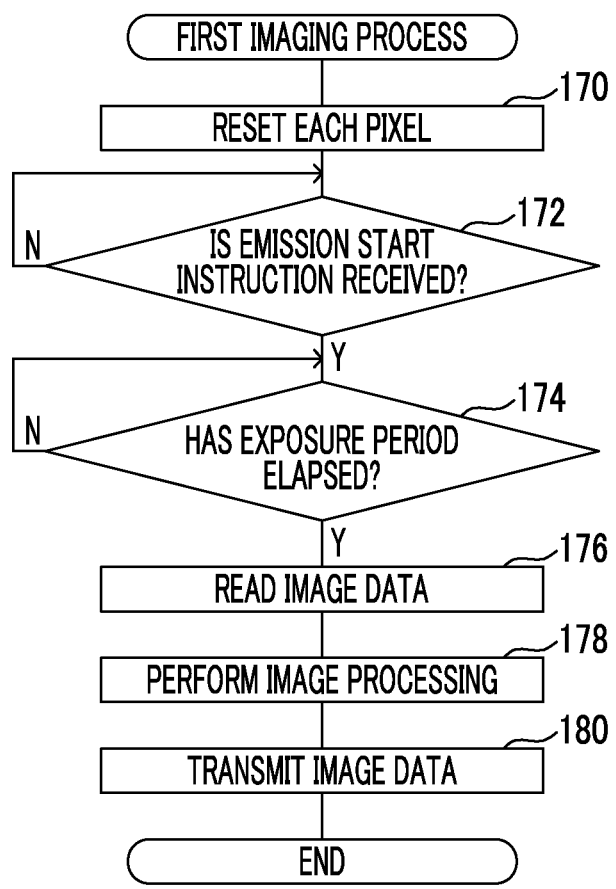
FIG. 12 is a flowchart illustrating the process flow of a first imaging processing program according to the first, third, and fourth embodiments.

FIG. 12 is a flowchart illustrating the process flow of a first imaging processing program that is executed by the control unit 58A of the radiography apparatus 16 in a case in which the radiography apparatus 16 is in an on state. The first imaging processing program is installed in a ROM of the memory 62 of the control unit 58A in advance.

Figure 13:
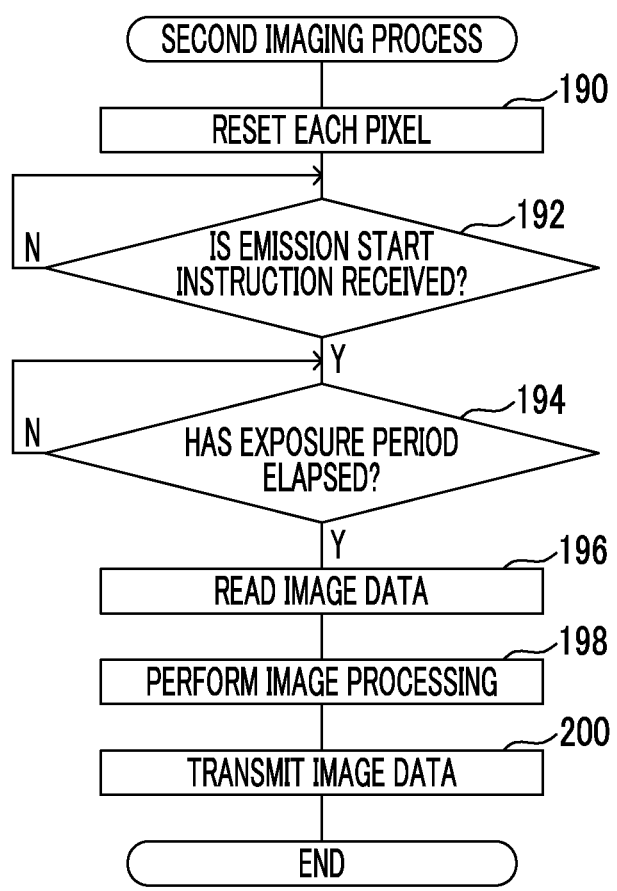
FIG. 13 is a flowchart illustrating the process flow of a second imaging processing program according to the first, third, and fourth embodiments.

FIG. 13 is a flowchart illustrating the process flow of a second imaging processing program that is executed by the control unit 58B of the radiography apparatus 16 in a case in which the radiography apparatus 16 is in the on state. The second imaging processing program is installed in a ROM of the memory 62 of the control unit 58B in advance.

Figure 14:
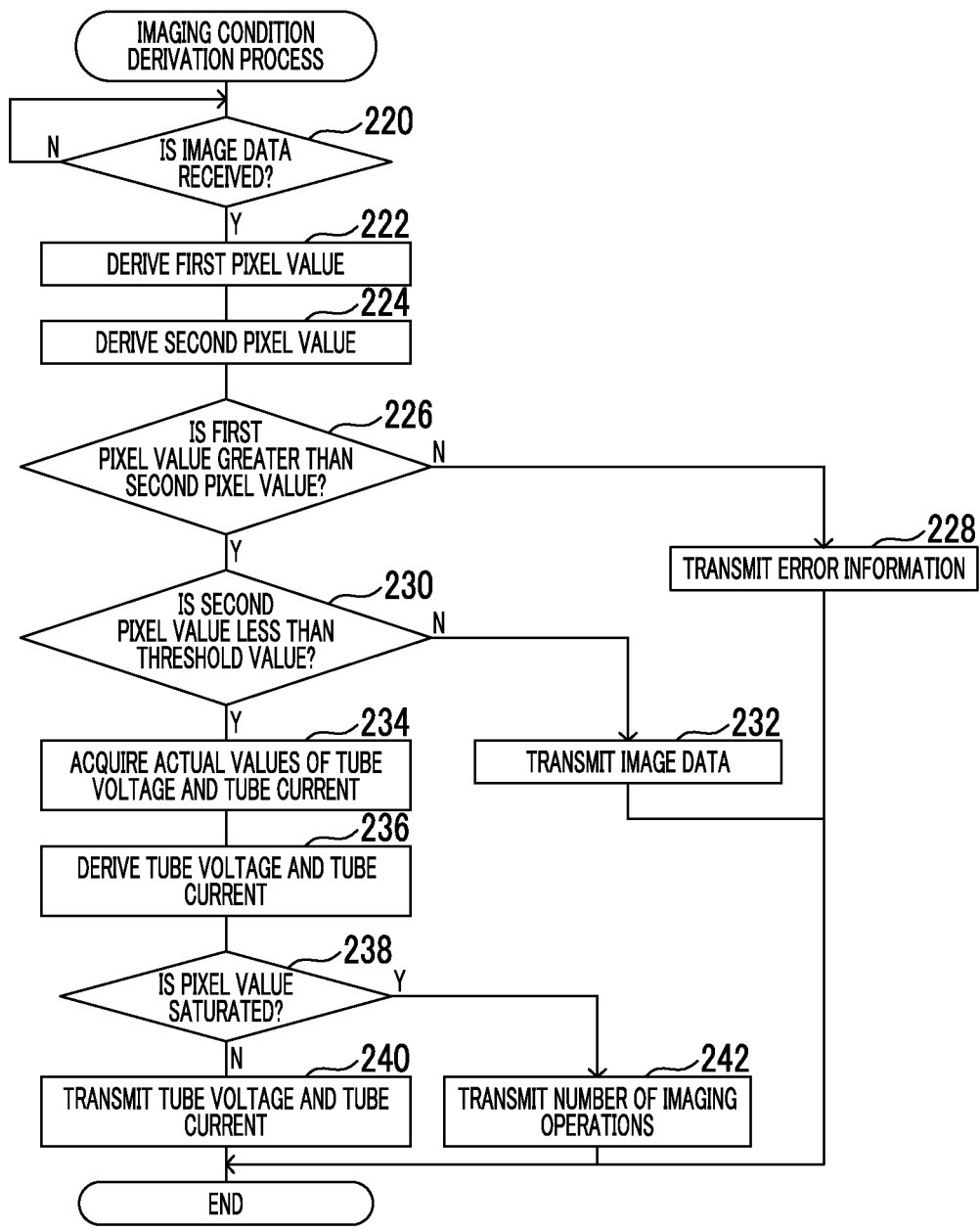
FIG. 14 is a flowchart illustrating the process flow of an imaging condition derivation processing program according to the first embodiment.

FIG. 14 is a flowchart illustrating the process flow of an imaging condition derivation processing program that is executed by the integrated control unit 71 of the radiography apparatus 16 in a case in which the radiography apparatus 16 is in the on state. The imaging condition derivation processing program is installed in a ROM of the memory 74 of the integrated control unit 71 in advance.

Hereinafter, the radiographic image captured by the first radiation detector 20A is referred to as a "first radiographic image" and image data indicating the first radiographic image is referred to as "first radiographic image data". In addition, hereinafter, the radiographic image captured by the second radiation detector 20B is referred to as a "second radiographic image" and image data indicating the second radiographic image is referred to as "second radiographic image data".

In Step 100 of FIG. 6, the CPU 80 transmits information included in the input imaging menu to the radiography apparatus 16 through the communication unit 92 and transmits the emission conditions of the radiation R to the radiation emitting apparatus 12 through the communication unit 92. Then, the CPU 80 transmits a command to start the emission of the radiation R to the radiography apparatus 16 and the radiation emitting apparatus 12 through the communication unit 92. When receiving the emission conditions and the emission start command transmitted from the console 18, the radiation emitting apparatus 12 starts the emission of the radiation R according to the received emission conditions. The radiation emitting apparatus 12 may comprise an irradiation button. In this case, the radiation emitting apparatus 12 receives the emission conditions and the emission start command transmitted from the console 18 and starts the emission of the radiation R according to the received emission conditions in a case in which the irradiation button is pressed.

Then, in Step 102, the CPU 80 waits until data transmitted by the radiography apparatus 16 is received. When the CPU 80 receives any one of error information, the first radiographic image data and the second radiographic image data, information indicating a tube voltage and a tube current, and imaging number information transmitted by the radiography apparatus 16, the determination result in Step 102 is "Yes" and the process proceeds to Step 104.

In Step 104, the CPU 80 determines whether the data received in Step 102 is two image data items, that is, the first radiographic image data and the second radiographic image data transmitted in Step 232 of an imaging condition derivation process which will be described below. In a case in which the determination result is "Yes", the process proceeds to Step 106. In Step 106, the CPU 80 performs an image generation process illustrated in FIG. 7 and then ends the overall imaging process.

Figure 7:
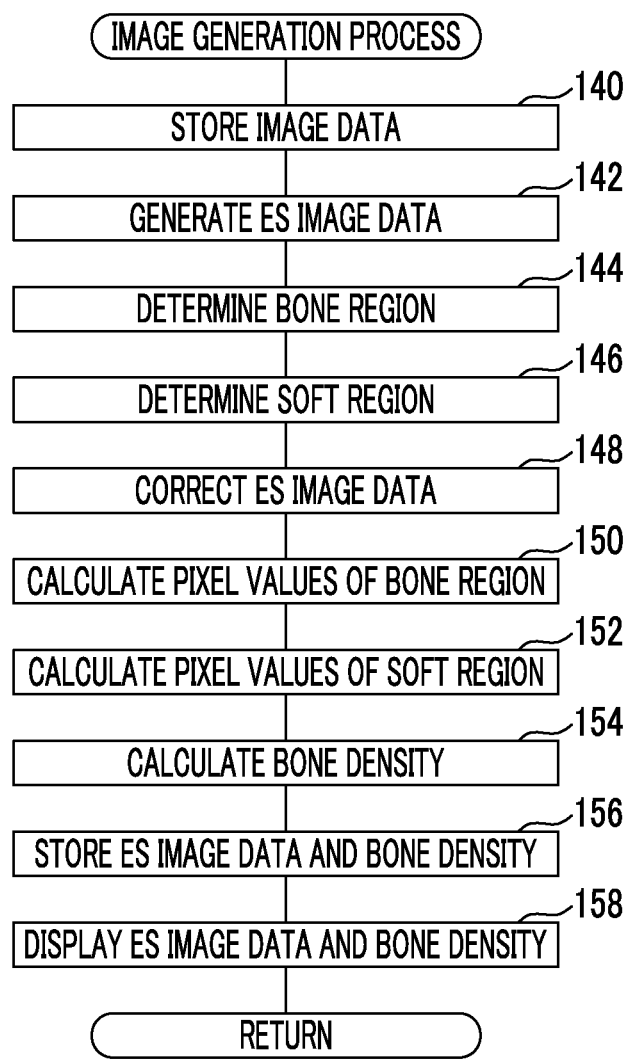
FIG. 7 is a flowchart illustrating the process flow of an image generation processing program according to each embodiment.

In Step 140 of FIG. 7, the CPU 80 stores the first radiographic image data and the second radiographic image data received in Step 102 in the storage unit 86. Then, in Step 142, the CPU 80 generates image data indicating an energy subtraction image, using the first radiographic image data and the second radiographic image data received in Step 102. Hereinafter, the energy subtraction image is referred to as an "ES image" and the image data indicating the energy subtraction image is referred to as "ES image data".

In this embodiment, the CPU 80 subtracts image data obtained by multiplying the first radiographic image data by a predetermined coefficient from image data obtained by multiplying the second radiographic image data by a predetermined coefficient for each corresponding pixel. The CPU 80 generates ES image data indicating an ES image in which soft tissues have been removed and bone tissues have been highlighted, using the subtraction. A method for determining the corresponding pixels of the first radiographic image data and the second radiographic image data is not particularly limited. For example, the amount of positional deviation between the first radiographic image data and the second radiographic image data, which are captured by the radiography apparatus 16 in a state in which a marker is put in advance, may be calculated from the difference between the positions of the marker in the first radiographic image data and the second radiographic image data. Then, the corresponding pixels of the first radiographic image data and the second radiographic image data may be determined on the basis of the calculated amount of positional deviation.

In this case, for example, the amount of positional deviation between the first radiographic image data and the second radiographic image data, which are obtained by capturing the image of both the subject W and the marker when the image of the subject W is captured, may be calculated from the difference between the positions of the marker in the first radiographic image data and the second radiographic image data. In addition, for example, the amount of positional deviation between the first radiographic image data and the second radiographic image data may be calculated on the basis of the structure of the subject W in the first radiographic image data and the second radiographic image data obtained by capturing the image of the subject W.

Then, in Step 144, the CPU 80 determines a bone tissue region (hereinafter, referred to as a "bone region") in the ES image that is indicated by the ES image data generated in Step 142. In this embodiment, for example, the CPU 80 estimates the approximate range of the bone region on the basis of the imaging part included in the imaging menu. Then, the CPU 80 detects pixels that are disposed in the vicinity of the pixels, of which the differential values are equal to or greater than a predetermined value, as the pixels forming the edge (end) of the bone region in the estimated range to determine the bone region.

Figure 8:
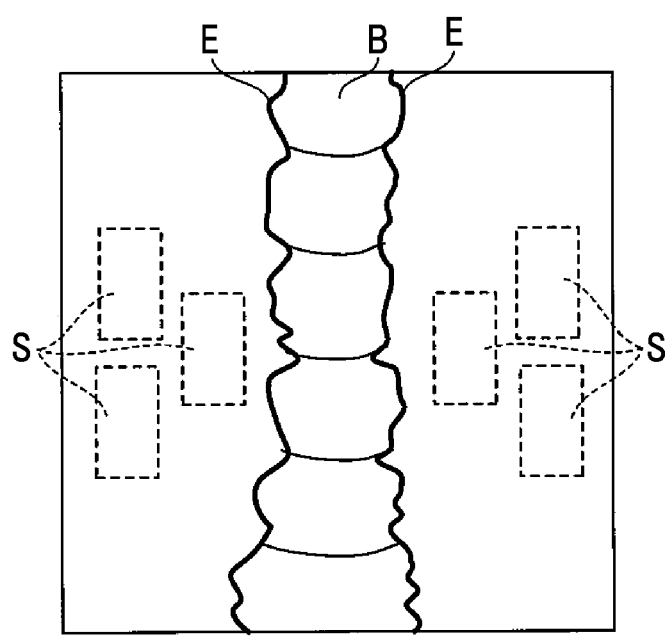
FIG. 8 is a front view schematically illustrating a bone tissue region and a soft tissue region.

For example, as illustrated in FIG. 8, in Step 144, the CPU 80 detects the edge E of a bone region B and determines a region in the edge E as the bone region B. For example, FIG. 8 illustrates an ES image in a case in which the image of a backbone part of the upper half of the body of the subject W is captured.

A method for determining the bone region B is not limited to the above-mentioned example. For example, the CPU 80 displays the ES image that is indicated by the ES image data generated in Step 142 on the display unit 88. The user designates the edge E of the bone region B in the ES image displayed on the display unit 88 through the operation panel 90. Then, the CPU 80 may determine a region in the edge E designated by the user as the bone region B.

The CPU 80 may display an image in which the ES image and the edge E detected in Step 144 overlap each other on the display unit 88. In this case, in a case in which it is necessary to correct the edge E displayed on the display unit 88, the user corrects the position of the edge E through the operation panel 90. Then, the CPU 80 may determine a region in the edge E corrected by the user as the bone region B.

Then, in Step 146, the CPU 80 determines a soft tissue region (hereinafter, referred to as a "soft region") in the ES image that is indicated by the ES image data generated in Step 142. In this embodiment, for example, the CPU 80 determines a region, which is other than the bone region B and has a predetermined area including pixels that are separated from the edge E by a distance corresponding to a predetermined number of pixels in a predetermined direction, as the soft region. For example, as illustrated in FIG. 8, in Step 146, the CPU 80 determines a plurality of (in the example illustrated in FIG. 8, six) soft regions S.

The predetermined direction and the predetermined number of pixels may be predetermined by, for example, experiments using the actual radiography apparatus 16 according to the imaging part. The predetermined area may be predetermined or may be designated by the user. In addition, for example, the CPU 80 may determine, as the soft region S, the pixels with pixel values in a predetermined range having the minimum pixel value (a pixel value corresponding to a position where the body thickness of the subject W is the maximum except the bone region B) as the lower limit in the ES image data. In addition, it goes without saying that the number of soft regions S determined in Step 146 is not limited to that illustrated in FIG. 8.

Then, in Step 148, the CPU 80 corrects the ES image data generated in Step 142 such that a variation in the ES image in each imaging operation is within an allowable range. In this embodiment, for example, the CPU 80 performs a correction process of removing image blur in the entire frequency band of the ES image data. The image data corrected in Step 148 is used to calculate bone density in a process from Step 150 to Step 154 which will be described below. Therefore, hereinafter, the corrected image data is referred to as "dual-energy X-ray absorptiometry (DXA) image data".

Then, in Step 150, the CPU 80 calculates an average value A1 of the pixel values of the bone region B in the DXA image data. Then, in Step 152, the CPU 80 calculates an average value A2 of the pixel values of all of the soft regions S in the DXA image data. Here, in this embodiment, for example, the CPU 80 performs weighting such that the soft region S which is further away from the edge E has a smaller pixel value and calculates the average value A2. Before the average values A1 and A2 are calculated in Step 150 and Step 152, respectively, abnormal values of the pixel values of the bone region B and the pixel values of the soft region S may be removed by, for example, a median filter.

Then, in Step 154, the CPU 80 calculates the bone density of the imaging part of the subject W. In this embodiment, for example, the CPU 80 calculates the difference between the average value A1 calculated in Step 150 and the average value A2 calculated in Step 152. In addition, the CPU 80 multiplies the calculated difference by a conversion coefficient for converting the pixel value into bone mass [g] to calculate the bone mass. Then, the CPU 80 divides the calculated bone mass by the area [cm$^2$] of the bone region B to calculate bone density [g/cm$^2$]. The conversion coefficient may be predetermined by, for example, experiments using the actual radiography apparatus 16 according to the imaging part.

Then, in Step 156, the CPU 80 stores the ES image data generated in Step 142 and the bone density calculated in Step 154 in the storage unit 86 so as to be associated with information for identifying the subject W. For example, in Step 156, the CPU 80 may store the first radiographic image data and the second radiographic image data received in Step 102 in the storage unit 86 so as to be associated with the information for identifying the subject W, instead of the ES image data and the bone density. In addition, for example, the CPU 80 may store the ES image data generated in Step 142, the bone density calculated in Step 154, and the first radiographic image data and the second radiographic image data received in Step 102 in the storage unit 86 so as to be associated with the information for identifying the subject W. Furthermore, for example, the CPU 80 may acquire the actual values of the tube voltage and the tube current of the radiation source 14 in the current imaging operation from the radiation source 14 and may store the acquired actual values in the storage unit 86 so as to be associated with the information for identifying the subject W.

Then, in Step 158, the CPU 80 displays the ES image indicated by the ES image data generated in Step 142 and the bone density calculated in Step 154 on the display unit 88 and then ends the image generation process.

On the other hand, in a case in which the determination result in Step 104 of FIG. 6 is "No", the process proceeds to Step 108. In Step 108, the CPU 80 determines whether the data received in Step 102 is information indicating the tube voltage and the tube current transmitted in Step 240 which will be described below. In a case in which the determination result is "Yes", the process proceeds to Step 110.

Figure 9:
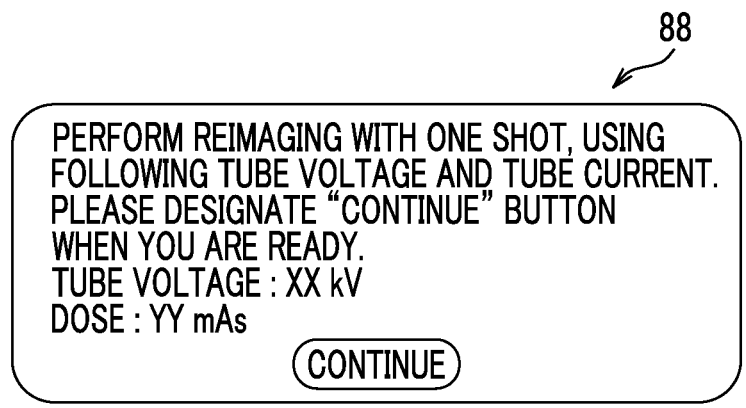
FIG. 9 is a diagram schematically illustrating an example of a first display screen according to the first and second embodiments.

In Step 110, the CPU 80 displays a first display screen, on which the tube voltage and the tube current indicated by information indicating the tube voltage and the tube current received in Step 102 are displayed, on the display unit 88. FIG. 9 illustrates an example of the first display screen. As illustrated in FIG. 9, information indicating that the same number of reimaging operations (in this embodiment, the number of reimaging operations is one. In the example illustrated in FIG. 9, one reimaging operation is represented by "one shot") as the number of imaging operations under the first imaging conditions is performed is displayed on the first display screen according to this embodiment. In addition, information indicating the tube voltage received in Step 102 is displayed on the first display screen. Furthermore, a value obtained by multiplying the tube current received in Step 102 by the same irradiation period as that in the first imaging conditions is displayed as the dose of the radiation R emitted from the radiation source 14 on the first display screen. In a case in which the user continues to capture a radiographic image, the user designates a "continue" button which is displayed in a lower part of the first display screen. When the "continue" button is designated, the process proceeds to Step 112.

Then, in Step 112, the CPU 80 corrects the tube voltage and the tube current received in Step 102 on the basis of the ratio of the set values to the actual values of the tube voltage and the tube current in the first imaging conditions and derives the set values of the tube voltage and the tube current under the second imaging conditions.

Then, in Step 114, the CPU 80 performs control for reimaging, using the tube voltage and the tube current derived in Step 112 and the same irradiation period as that in the first imaging conditions and then ends the overall imaging process. Specifically, the CPU 80 performs the same process as that in Step 100, using the tube voltage and the tube current derived in Step 112 and the same irradiation period as that in the first imaging conditions. Then, the radiography apparatus 16 performs a first imaging process and a second imaging process which will be described below and the first radiographic image data and the second radiographic image data are transmitted from the radiography apparatus 16 to the console 18. When receiving the first radiographic image data and the second radiographic image data, the CPU 80 performs the same process as the image generation process to generate ES image data and to derive bone density. In this case, in the image generation process, the CPU 80 may store at least one of the first radiographic image data, the second radiographic image data, or the actual values of the tube voltage and the tube current obtained by imaging under the first imaging conditions in the storage unit 86 in Step 156.

On the other hand, in a case in which the determination result in Step 108 is "No", the process proceeds to Step 116. In Step 116, the CPU 80 determines whether the data received in Step 102 is the imaging number information transmitted in Step 242 of an imaging condition derivation process which will be described below. In a case in which the determination result is "Yes", the process proceeds to Step 118.

Figure 10:
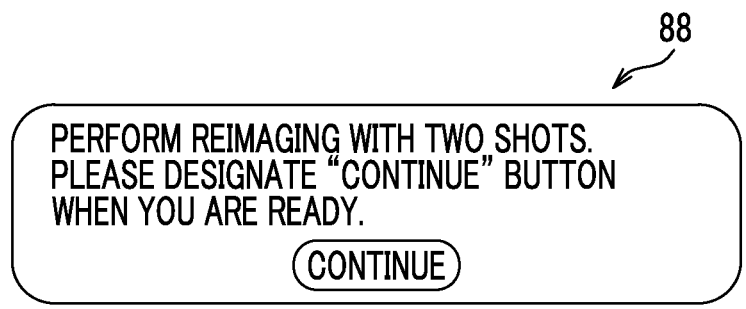
FIG. 10 is a diagram schematically illustrating an example of a second display screen according to the first and second embodiments.

In Step 118, the CPU 80 displays a second display screen, on which the number of imaging operations indicated by the imaging number information received in Step 102 is displayed, on the display unit 88. FIG. 10 illustrates an example of the second display screen. As illustrated in FIG. 10, information indicating that the same number of reimaging operations as the number of imaging operations (in this embodiment, the number of imaging operations is two. In the example illustrated in FIG. 10, the number of imaging operations is represented by "two shots") indicated by the imaging number information received in Step 102 is performed is displayed on the second display screen according to this embodiment. In a case in which the user continues to capture a radiographic image, the user designates a "continue" button which is displayed in a lower part of the second display screen. When the "continue" button is designated, the process proceeds to Step 120.

In Step 120, the CPU 80 performs control for performing reimaging and then ends the overall imaging process. Specifically, first, the CPU 80 performs control for capturing a radiographic image under the same emission condition as that in the first imaging conditions and receives the first radiographic image data captured by the first radiation detector 20A. Then, the CPU 80 performs control for capturing a radiographic image at a higher tube voltage than that in the first imaging conditions and receives the first radiographic image data captured by the first radiation detector 20A.

In the reimaging process in Step 122, since imaging is performed two times, the subject W is likely to move during the two imaging operations. Therefore, in this embodiment, first, the CPU 80 derives the amount of positional deviation of the subject W between two first radiographic images indicated by the received two first radiographic image data items.

Specifically, for example, the CPU 80 extracts a plurality of analysis points from the edge of the bone region in each of the two first radiographic images, calculates the average value of the amounts of positional deviation between the corresponding analysis points, and derives the amount of positional deviation of the subject W between the two first radiographic images. A known method, such as a method disclosed in JP2014-079558A, may be used as a process of extracting the analysis points. Therefore, the description of the process of extracting the analysis points will be omitted.

Then, in a case in which the derived amount of positional deviation is less than a predetermined threshold value, the CPU 80 performs the image generation process, using the received two first radiographic image data items, to generate ES image data and to derive bone density. On the other hand, in a case in which the derived amount of positional deviation is equal to or greater than the threshold value, the CPU 80 performs a process of aligning the position of the subject W between the two first radiographic images. A known method, such as a method disclosed in JP1998-108073A (JP-H10-108073A), may be applied as the alignment process. Therefore, the description of the alignment process will be omitted. In this case, the CPU 80 performs the image generation process, using two image data items obtained by performing the alignment process for the two first radiographic image data items, to generate ES image data and to derive bone density.

In Step 242 of the imaging condition derivation process which will be described below, in a case in which the radiography apparatus 16 transmits the tube voltage and the tube current in addition to the imaging number information, the tube voltage and the tube current may be set to the radiation source 14 and a first radiographic image capture operation may be performed. In the image generation process, the CPU 80 may store at least one of the first radiographic image data, the second radiographic image data, or the actual values of the tube voltage and the tube current obtained by imaging under the first imaging conditions in the storage unit 86 in Step 156.

On the other hand, in a case in which the determination result in Step 116 is "No", the data received in Step 102 is regarded as error information which is transmitted in Step 228 of the imaging condition derivation process which will be described below and the process proceeds to Step 122.

Figure 11:
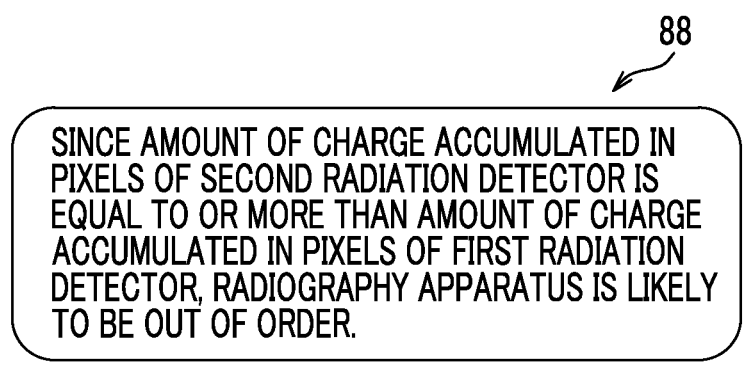
FIG. 11 is a diagram schematically illustrating an example of an error notification screen according to the first, second, and fourth embodiments.

In Step 122, the CPU 80 displays an error notification screen on the display unit 88 and then ends the overall imaging process. FIG. 11 illustrates an example of the error notification screen. As illustrated in FIG. 11, information indicating that the amount of charge accumulated in the pixels 32 of the second radiation detector 20B is equal to or more than the amount of charge accumulated in the pixels 32 of the first radiation detector 20A and that the radiography apparatus 16 is likely to be out of order is displayed on the error notification screen according to this embodiment.

In Step 170 of FIG. 12, the control unit 58A performs a reset operation of extracting and removing the charge accumulated in the sensor unit 32A of each pixel 32 in the first radiation detector 20A. In addition, the control unit 58A may perform the reset operation in Step 170 only once, may repeat the reset operation a predetermined number of times, or may repeat the reset operation until the determination result in Step 172, which will be described below, is "Yes".

Then, in Step 172, the control unit 58A waits for the reception of a command to start the emission of the radiation R. When the control unit 58A receives the emission start command transmitted from the console 18 in Step 100 of the overall imaging process through the communication unit 66, the determination result in Step 172 is "Yes" and the process proceeds to Step 174. In a case in which the radiation emitting apparatus 12 comprises an irradiation button, when the control unit 58A receives the emission start command transmitted from the console 18 and information indicating that the irradiation button has been pressed through the communication unit 66, the determination result in Step 172 is "Yes". In this case, for example, in a case in which the irradiation button is pressed, the radiation emitting apparatus 12 may directly transmit the information indicating that the irradiation button has been pressed to the radiography apparatus 16 or may transmit the information to the radiography apparatus 16 through the console 18.

In Step 174, the control unit 58A waits for the irradiation period included in the information transmitted from the console 18 in Step 100 of the overall imaging process.

In Step 176, the control unit 58A controls the gate line driver 52A such that the gate line driver 52A sequentially outputs an on signal to each gate line 34 of the first radiation detector 20A for a predetermined period. Then, each line of the thin film transistors 32B connected to each gate line 34 is sequentially turned on and the charge accumulated in each line of the sensor unit 32A sequentially flows as an electric signal to each data line 36. Then, the electric signal that flows to each data line 36 is converted into digital image data by the signal processing unit 54A and is then stored in the image memory 56A.

Then, in Step 178, the control unit 58A performs image processing including various correction processes, such as offset correction and gain correction, for the image data stored in the image memory 56A in Step 176. Then, in Step 180, the control unit 58A transmits the image data (first radiographic image data) processed in Step 178 to the integrated control unit 71 and then ends the first imaging process.

In Step 190 of FIG. 13, the control unit 58B performs a reset operation of extracting and removing the charge accumulated in the sensor unit 32A of each pixel 32 in the second radiation detector 20B. In addition, the control unit 58B may perform the reset operation in Step 190 only once, may repeat the reset operation a predetermined number of times, or may repeat the reset operation until the determination result in Step 192, which will be described below, is "Yes".

Then, in Step 192, the control unit 58B waits until a command to start the emission of the radiation R is received. When the control unit 58B receives the emission start command transmitted from the console 18 in Step 100 of the overall imaging process through the communication unit 66, the determination result in Step 192 is "Yes" and the process proceeds to Step 194. In a case in which the radiation emitting apparatus 12 comprises an irradiation button, when the control unit 58B receives the emission start command transmitted from the console 18 and information indicating that the irradiation button has been pressed through the communication unit 66, the determination result in Step 192 is "Yes". In this case, for example, in a case in which the irradiation button is pressed, the radiation emitting apparatus 12 may directly transmit the information indicating that the irradiation button has been pressed to the radiography apparatus 16 or may transmit the information to the radiography apparatus 16 through the console 18.

In Step 194, the control unit 58B waits for the irradiation period included in the information transmitted from the console 18 in Step 100 of the overall imaging process.

In Step 196, the control unit 58B controls the gate line driver 52B such that the gate line driver 52B sequentially outputs an on signal to each gate line 34 of the second radiation detector 20B for a predetermined period. Then, each line of the thin film transistors 32B connected to each gate line 34 is sequentially turned on and the charge accumulated in each line of the sensor unit 32A sequentially flows as an electric signal to each data line 36. Then, the electric signal that flows to each data line 36 is converted into digital image data by the signal processing unit 54B and is then stored in the image memory 56B.

Then, in Step 198, the control unit 58B performs image processing including various correction processes, such as offset correction and gain correction, for the image data stored in the image memory 56B in Step 196. Then, in Step 200, the control unit 58B transmits the image data (second radiographic image data) processed in Step 198 to the integrated control unit 71 and then ends the second imaging process.

In Step 220 of the imaging condition derivation process illustrated in FIG. 14, the integrated control unit 71 waits until the first radiographic image data and the second radiographic image data are received. When the integrated control unit 71 receives the first radiographic image data transmitted in Step 180 and the second radiographic image data transmitted in Step 200, the determination result in Step 220 is "Yes" and the process proceeds to Step 222.

In Step 222, the integrated control unit 71 derives the average value (hereinafter, referred to as a "first pixel value") of the pixel values of the first radiographic image indicated by the first radiographic image data received in Step 220. In this embodiment, for example, the integrated control unit 71 derives, as the first pixel value, the average value of the pixel values of the pixels 32 in a region through which the radiation R is transmitted in the first radiographic image data. For example, a region of interest (ROI) which is designated by the user in advance can be applied to the region through which the radiation R is transmitted.

Then, in Step 224, the integrated control unit 71 derives the average value (hereinafter, referred to as a "second pixel value") of the pixel values of the second radiographic image indicated by the second radiographic image data received in Step 220. In this embodiment, for example, the integrated control unit 71 derives, as the second pixel value, the average value of the pixel values of the pixels 32 in a region through which the radiation R is transmitted in the second radiographic image data, similarly to Step 222. It goes without saying that the region in which the average value of the pixel values is derived in Step 222 and Step 224 is not limited to the region in which the radiation R is transmitted. For example, the region in which the average value of the pixel values is derived in Step 222 and Step 224 may be set by the user.

Then, in Step 226, the integrated control unit 71 determines whether the first pixel value derived in Step 222 is greater than the second pixel value derived in Step 224. In a case in which the determination result is "No", the process proceeds to Step 228.

As described above, since the radiation R emitted to the radiography apparatus 16 is absorbed by the first radiation detector 20A, the amount of radiation that reaches the second radiation detector 20B is less than the amount of radiation that reaches the first radiation detector 20A. That is, in a case in which the radiography apparatus 16 is in a normal state, the first pixel value derived in Step 222 is greater than the second pixel value derived in Step 224.

Here, in Step 228, the integrated control unit 71 transmits error information indicating that the amount of radiation that reaches the second radiation detector 20B is equal to or more than the amount of radiation that reaches the first radiation detector 20A to the console 18 through the communication unit 66 and then ends the imaging condition derivation process.

On the other hand, in a case in which the determination result in Step 226 is "Yes", the process proceeds to Step 230. In Step 230, the integrated control unit 71 determines whether the second pixel value derived in Step 224 is less than a predetermined threshold value TH1. For example, a value which is obtained as the lower limit at which the quality of the ES image and the accuracy of bone density obtained in Step 106 are within the allowable range by experiments using the actual radiography apparatus 16 may be applied as the threshold value TH1. For example, in this embodiment, the pixel value of the pixel 32 in a case in which the amount of radiation is 0.1 [mR] is used as the threshold value TH1.

For example, in Step 230, the integrated control unit 71 may determine whether both the second pixel value derived in Step 224 and the first pixel value derived in Step 222 are less than the threshold value TH1. In this case, the threshold values to be compared with the first pixel value and the second pixel value may be different from each other. In this case, for example, the threshold value to be compared with the first pixel value is greater than the threshold value to be compared with the second pixel value.

For example, in Step 230, the integrated control unit 71 may estimate the second pixel value from the first pixel value derived in Step 222 and may determine whether the estimated second pixel value is less than the threshold value TH1. In this case, for example, the integrated control unit 71 may derive, as the second pixel value, a value obtained by multiplying the first pixel value derived in Step 222 by predetermined transmittance. In this case, for example, a ratio obtained by dividing the amount of radiation that reaches the second radiation detector 20B by the amount of radiation that reaches the first radiation detector 20A, which is obtained by experiments using the actual radiography apparatus 16, may be used as the transmittance. For example, in Step 230, the integrated control unit 71 may determine whether the first pixel value is less than a value obtained by dividing the threshold value TH1 by the transmittance.

In a case in which the determination result in Step 230 is "No", the process proceeds to Step 232. In Step 232, the integrated control unit 71 transmits the first radiographic image data and the second radiographic image data received in Step 220 to the console 18 through the communication unit 66 and then ends the imaging condition derivation process.

On the other hand, in a case in which the determination result in Step 230 is "Yes", the process proceeds to Step 234. In Step 234, the integrated control unit 71 acquires the actual values of the tube voltage and the tube current of the radiation source 14 in the current imaging operation from the radiation source 14 through the console 18.

Then, in Step 236, the integrated control unit 71 derives, as the second imaging conditions, the tube voltage and the tube current at which the second pixel value is equal to or greater than the threshold value TH1 in a case in which the irradiation period and the number of imaging operations are the same as the irradiation period and the number of imaging operations in the first imaging conditions. Specifically, for example, the integrated control unit 71 multiplies a ratio, which is obtained by dividing a threshold value TH1 by the first pixel value derived in Step 222, by the actual value of the tube current acquired in Step 234 to derive the tube current in the second imaging conditions. In this case, the integrated control unit 71 may add a predetermined margin to the derived tube current.

In a case in which the derived tube current is equal to or less than the upper limit of the tube current that can be set to the radiation source 14, the integrated control unit 71 uses the tube voltage in the second imaging conditions as the tube voltage acquired in Step 234. On the other hand, in a case in which the derived tube current is greater than the upper limit of the tube current that can be set to the radiation source 14, the integrated control unit 71 uses the tube voltage in the second imaging conditions as the upper limit of the tube current that can be set to the radiation source 14. In this case, the integrated control unit 71 derives a tube voltage, which is obtained by increasing the tube voltage acquired in Step 234 by a value that corresponds to the amount of radiation corresponding to the difference between the derived tube current and the upper limit of the tube current, as the tube voltage in the second imaging conditions.

As illustrated in FIG. 5, the difference between the amounts of energy of the radiation R absorbed by the radiation detectors 20 decreases after a peak value as the energy of the radiation R increases. That is, as the tube voltage of the radiation source 14 increases, the difference between the amounts of energy of the radiation R absorbed by the radiation detectors 20 decreases. As the difference decreases, an image difference that is useful as an ES image is less likely to occur between the images captured by each radiation detector 20. Therefore, in this embodiment, the condition in which the tube current is preferentially increased over the tube voltage is applied as the second imaging conditions.

Then, in Step 238, in a case in which the tube voltage and the tube current derived in Step 236 are set to the radiation source 14 and radiographic images are captured, the integrated control unit 71 determines whether the pixel value of the first radiographic image data is saturated. Specifically, the integrated control unit 71 derives the following estimated value from the pixel value of each pixel in the first radiographic image data received in Step 220 and the actual values of the tube voltage and the tube current acquired in Step 234. That is, the integrated control unit 71 derives, from the pixel value of each pixel and the actual values, the estimated value of the pixel value of each pixel in the first radiographic image data in a case in which the tube voltage and the tube current derived in Step 236 are set to the radiation source 14 and radiographic images are captured.

Then, the integrated control unit 71 determines whether the derived estimated value of the pixel value of each pixel is greater than the upper limit of the pixel value to determine whether the pixel value of the first radiographic image data is saturated. In a case in which the determination result is "Yes", the process proceeds to Step 242. In a case in which the determination result is "No", the process proceeds to Step 240.

In Step 240, the integrated control unit 71 transmits information indicating the tube voltage and the tube current derived in Step 236 as the second imaging conditions to the console 18 through the communication unit 66 and then ends the imaging condition derivation process. In Step 242, the integrated control unit 71 transmits imaging number information indicating that a plurality of imaging operations (two imaging operations in this embodiment) are performed as the second imaging conditions to the console 18 through the communication unit 66 and then ends the imaging condition derivation process.

In Step 242, for example, in a case in which the first pixel value derived in Step 222 is less than the threshold value TH1, the integrated control unit 71 may derive the tube voltage and the tube current at which the first pixel value is equal to or greater than the threshold value TH1, similarly to Step 236. In this case, in addition to the imaging number information, the integrated control unit 71 transmits the derived tube voltage and the derived tube current to the console 18 through the communication unit 66.

As described above, according to this embodiment, in a case in which the second pixel value is less than the threshold value TH1, the tube voltage and the tube current at which the second pixel value is equal to or greater than the threshold value TH1 in a case in which the number of imaging operations is equal to that in the first imaging conditions are derived as the second imaging conditions. Therefore, in a case in which the amount of radiation in imaging under the first imaging conditions is insufficient to capture a radiographic image, it is possible to newly apply appropriate second imaging conditions.

In this embodiment, an example in which the tube voltage and the tube current are increased in a case in which the second pixel value is less than the threshold value TH2 has been described. However, the invention is not limited thereto. For example, the gain of the amplifying circuits of the signal processing units 54A and 54B may be increased.

In this embodiment, instead of the first pixel value, a signal/noise (S/N) ratio which is the ratio of the electric signal output from the first radiation detector 20A to the amount of noise may be used. In this case, for example, the ratio of the first pixel value to a value (for example, standard deviation) indicating the degree of variation in the pixel from which the first pixel value is to be derived is applied as the S/N ratio. In addition, in this case, instead of the second pixel value, similarly, for example, an S/N ratio which is the ratio of the electric signal output from the second radiation detector 20B to the amount of noise is used.

In this embodiment, in a case in which the second pixel value is equal to or greater than the threshold value TH1, it may be determined whether the difference between the first pixel value and the second pixel value is less than a threshold value. In this case, in a case in which the difference is equal to or greater than the threshold value, the first radiographic image data and the second radiographic image data are transmitted to the console 18 in Step 232. In a case in which the difference is less than the threshold value, for example, as the tube voltage in the second imaging conditions, a tube voltage that is higher than the tube voltage in the first imaging conditions is derived. In this case, for example, a value that is obtained as the lower limit at which an image difference useful as an ES image occurs by experiments using the actual radiography apparatus 16 may be applied as the threshold value.

In this embodiment, in Step 230, it may be determined whether the difference between the first signal and the second signal (that is, the difference between the first pixel value and the second pixel value) is less than a threshold value. For example, in a case in which a metal plate is inserted into an imaging part of the subject W, the difference between the first signal and the second signal is relatively small and the amount of radiation that reaches the second radiation detector 20B is relatively small. In this case, the second imaging conditions may be derived in a case in which the difference between the first signal and the second signal is less than the threshold value.

In this embodiment, in Step 230, predetermined image processing, such as a process of detecting a bone region of the subject W, may be performed for the second radiographic image that is indicated by the second radiographic image data received in Step 220. In this case, for example, in a case in which the image processing ends normally, the determination result in Step 230 is "No". In a case in which the image processing ends abnormally, the determination result in Step 230 is "Yes".

In this embodiment, in a case in which it is determined in Step 238 that the first pixel value is saturated, the gain of the amplifying circuits of the signal processing units 54A and 54B may be reduced.

In this embodiment, the case in which the irradiation period in the second imaging conditions is the same as the irradiation period in the first imaging conditions has been described. However, the invention is not limited thereto. For example, the irradiation period in the second imaging conditions may be different from the irradiation period in the first imaging conditions. In this case, for example, in Step 236, the integrated control unit 71 derives, as the second imaging conditions, the irradiation period for which the second pixel value is equal to or greater than the threshold value TH1 in a case in which the tube voltage, the tube current, and the number of imaging operations are equal to the tube voltage, the tube current, and the number of imaging operations in the first imaging conditions, respectively. In addition, in this case, in Step 114, the CPU 80 performs control for reimaging, using the same tube voltage and tube current as those in the first imaging conditions and the irradiation period derived by the integrated control unit 71.

Second Embodiment

Hereinafter, a second embodiment of the invention will be described in detail. Since a radiography system 10 according to this embodiment has the same structure as the radiography system according to the first embodiment except for the structure of a main portion of an electric system of a radiography apparatus 16 (see FIG. 1, FIG. 2, and FIG. 4), the description thereof will not be repeated here. In addition, components having the same functions as those in the first embodiment are denoted by the same reference numerals and the description thereof will not be repeated.

First, the structure of the main portion of the electric system of the radiography apparatus 16 according to this embodiment will be described with reference to FIG. 15.

Figure 15:
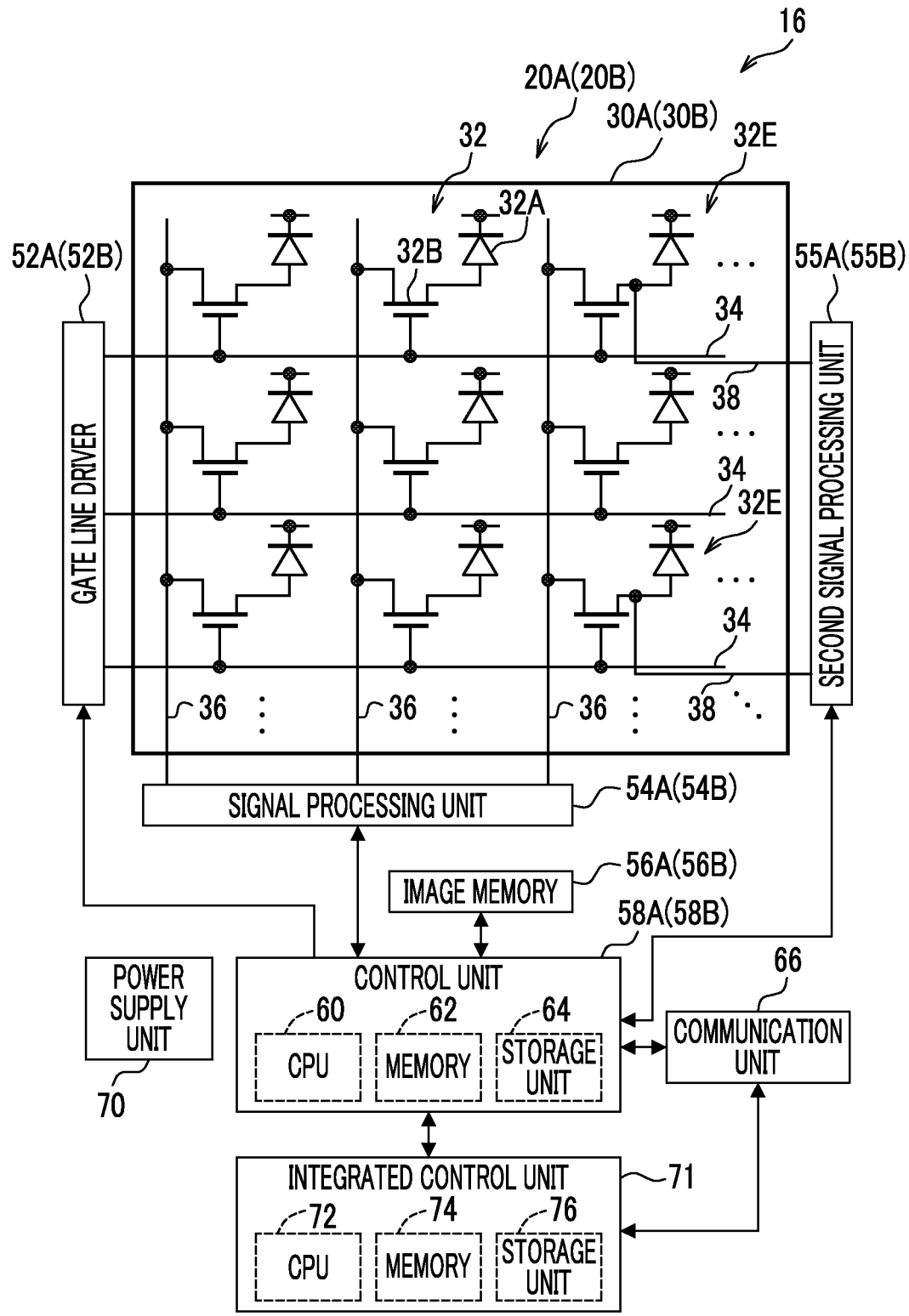
FIG. 15 is a block diagram illustrating an example of the structure of a main portion of an electric system of a radiography apparatus according to the second embodiment.

As illustrated in FIG. 15, the radiography apparatus 16 according to this embodiment differs from the radiography apparatus according to the first embodiment in that some of the pixels 32 provided on the TFT substrates 30A and 30B are substituted with pixels 32E for detecting the emission of the radiation R. In addition, a radiation detector 20A according to this embodiment further comprises a second signal processing unit 55A that is opposite to the gate line driver 52A, with the TFT substrate 30A interposed therebetween. The arrangement state of the pixels 32E is not particularly limited. For example, the pixels 32E may be arranged so as to be uniformly distributed on the entire TFT substrate 30A. In addition, for example, the pixels 32E may be arranged in a partial region including the center of an imaging region of the radiation detector 20A (for example, a rectangular region including a predetermined number of pixels which has, as the center, the pixel 32 disposed at the center of the TFT substrate 30A).

Similarly to the pixel 32, the pixel 32E includes a sensor unit 32A and a thin film transistor 32B. In addition, one end of a direct read line 38 is connected to a connection portion between the sensor unit 32A and the thin film transistor 32B forming the pixel 32E.

The other end of the direct read line 38 is connected to the second signal processing unit 55A. The second signal processing unit 55A comprises an amplifier (not illustrated) and an A/D converter (not illustrated) which are provided for each direct read line 38 and is connected to the control unit 58A. The second signal processing unit 55A performs sampling for each direct read line 38 in a predetermined cycle to convert electric signals transmitted through each direct read line 38 into digital data and sequentially outputs the digital data to the control unit 58A, under the control of the control unit 58A. The digital data indicates the amount of radiation and the control unit 58A controls the second signal processing unit 55A such that the amount of radiation emitted to the first radiation detector 20A is sequentially detected.

Since components of pixels 32E, direct read lines 38, and a second signal processing unit 55B on the TFT substrate 30B of the second radiation detector 20B are the same as the corresponding components of the first radiation detector 20A, the description thereof will not be repeated here.

In this embodiment, a case in which an accumulation value of the amount of radiation emitted to the first radiation detector 20A, which is sequentially detected by the control of the second signal processing unit 55A by the control unit 58A, is applied as the first electric signal will be described. In addition, a case in which an accumulation value of the amount of radiation emitted to the second radiation detector 20B, which is sequentially detected by the control of the second signal processing unit 55B by the control unit 58B, is applied as the second electric signal will be described.

Next, the operation of the radiography system 10 according to this embodiment will be described with reference to FIGS. 16 to 18. Since the process flow of an overall imaging processing program and an image generation processing program according to this embodiment is the same as that in the first embodiment (see FIGS. 6 and 7), the description thereof will not be repeated here.

Figure 16:
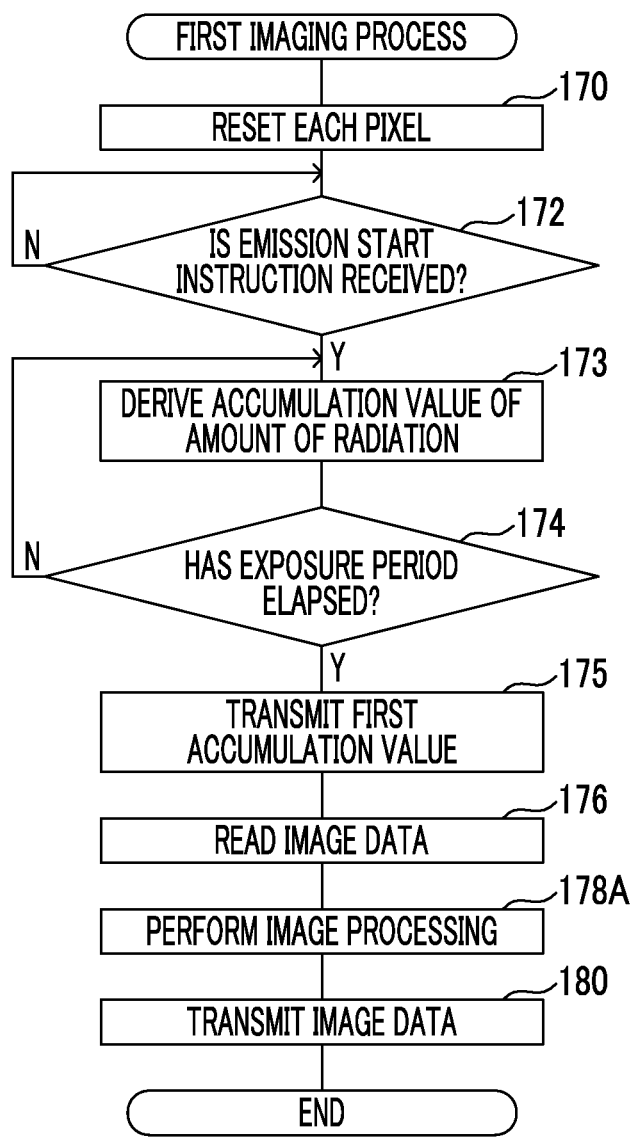
FIG. 16 is a flowchart illustrating the process flow of a first imaging processing program according to the second embodiment.

FIG. 16 is a flowchart illustrating the process flow of a first imaging processing program that is executed by the control unit 58A of the radiography apparatus 16 in a case in which the radiography apparatus 16 is in an on state. The first imaging processing program is installed in the ROM of the memory 62 of the control unit 58A in advance. In FIG. 16, steps in which the same processes as those in FIG. 12 are performed are denoted by the same step numbers as those in FIG. 12 and the description thereof will not be repeated.

Figure 17:
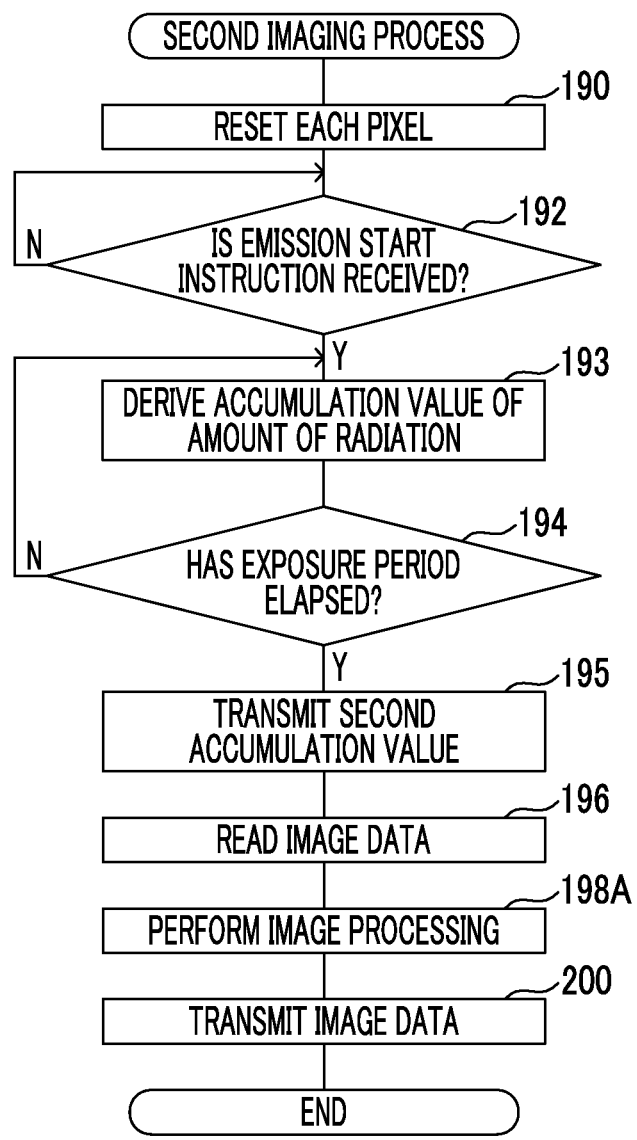
FIG. 17 is a flowchart illustrating the process flow of a second imaging processing program according to the second embodiment.

FIG. 17 is a flowchart illustrating the process flow of a second imaging processing program that is executed by the control unit 58B of the radiography apparatus 16 in a case in which the radiography apparatus 16 is in the on state. The second imaging processing program is installed in the ROM of the memory 62 of the control unit 58B in advance. In FIG. 17, steps in which the same processes as those in FIG. 13 are performed are denoted by the same step numbers as those in FIG. 13 and the description thereof will not be repeated.

Figure 18:
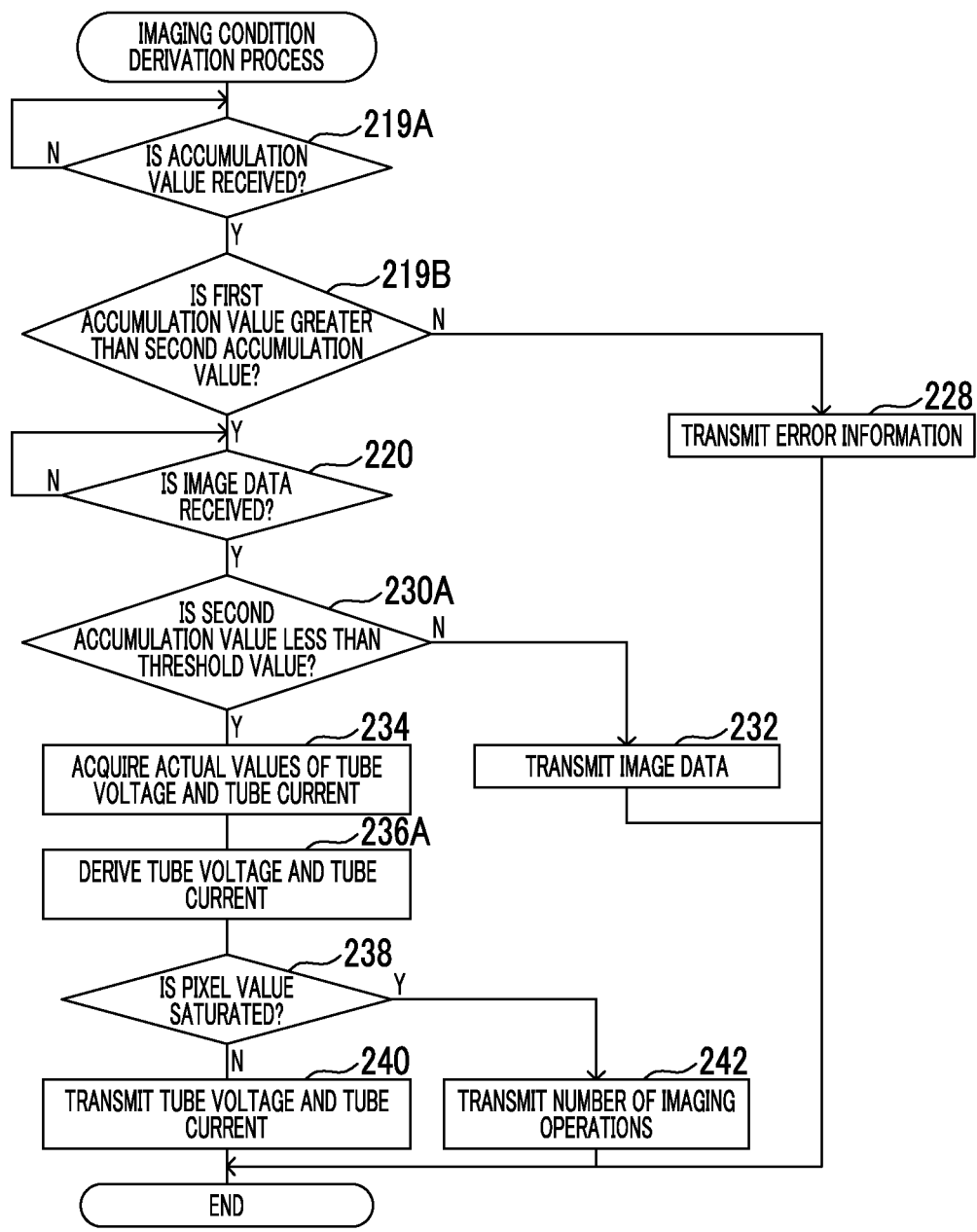
FIG. 18 is a flowchart illustrating the process flow of an imaging condition derivation processing program according to the second embodiment.

FIG. 18 is a flowchart illustrating the process flow of an imaging condition derivation processing program that is executed by the integrated control unit 71 of the radiography apparatus 16 in a case in which the radiography apparatus 16 is in the on state. The imaging condition derivation processing program is installed in the ROM of the memory 74 of the integrated control unit 71 in advance. In FIG. 18, steps in which the same processes as those in FIG. 14 are performed are denoted by the same step numbers as those in FIG. 14 and the description thereof will not be repeated.

In Step 173 of FIG. 16, the control unit 58A controls the second signal processing unit 55A such that digital data indicating the amount of radiation output from the second signal processing unit 55A is acquired and derives the accumulation value of the acquired digital data. Hereinafter, the accumulation value derived in Step 173 is referred to as a "first accumulation value".

The control unit 58A repeatedly performs Step 173 until the determination result in Step 174 is "Yes". In Step 175, the control unit 58A transmits the first accumulation value derived in Step 173 to the integrated control unit 71. In Step 178A, the control unit 58A performs image processing including various correction processes, such as offset correction and gain correction, for the image data stored in the image memory 56A in Step 176, similarly to Step 178. In addition, the control unit 58A performs a defective pixel correction process of interpolating pixel information of a radiographic image at the arrangement position of the pixel 32E with pixel information obtained by the pixels 32 located in the vicinity of the pixel 32E.

In Step 193 of FIG. 17, the control unit 58B controls the second signal processing unit 55B such that digital data indicating the amount of radiation output from the second signal processing unit 55B is acquired and derives the accumulation value of the acquired digital data. Hereinafter, the accumulation value derived in Step 193 is referred to as a "second accumulation value".

The control unit 58B repeatedly performs Step 193 until the determination result in Step 194 is "Yes". In Step 195, the control unit 58B transmits the second accumulation value derived in Step 193 to the integrated control unit 71. In Step 198A, the control unit 58B performs image processing including various correction processes, such as offset correction and gain correction, for the image data stored in the image memory 56B in Step 196, similarly to Step 198. In addition, the control unit 58B performs a defective pixel correction process of interpolating pixel information of a radiographic image at the arrangement position of the pixel 32E with pixel information obtained by the pixels 32 located in the vicinity of the pixel 32E.

In Step 219A of FIG. 18, the integrated control unit 71 waits until the first accumulation value and the second accumulation value are received. When the integrated control unit 71 receives the first accumulation value transmitted in Step 175 and the second accumulation value transmitted in Step 195, the determination result in Step 219A is "Yes" and the process proceeds to Step 219B.

In Step 219B, the integrated control unit 71 determines whether the first accumulation value received in Step 219A is greater than the second accumulation value received in Step 219A. In a case in which the determination result is "No", the process proceeds to Step 228. In a case in which the determination result is "Yes", the process proceeds to Step 220.

In Step 230A, the integrated control unit 71 determines whether the second accumulation value received in Step 219A is less than a predetermined threshold value TH2. For example, a value which is predetermined as the value at which the quality of the ES image and the accuracy of the bone density obtained in Step 106 are in the allowable range by experiments using the actual radiography apparatus 16 may be applied as the threshold value TH2. For example, in this embodiment, the second accumulation value in a case in which the amount of radiation is 0.1 [mR] is used as the threshold value TH2.

For example, in Step 230A, the integrated control unit 71 may determine whether both the first accumulation value and the second accumulation value received in Step 219A are less than the threshold value TH2. In this case, the threshold values to be compared with the first accumulation value and the second accumulation value may be different from each other. In this case, for example, the threshold value to be compared with the first accumulation value is greater than the threshold value to be compared with the second accumulation value.

For example, in Step 230A, the integrated control unit 71 may estimate the second accumulation value from the first accumulation value received in Step 219A and may determine whether the estimated second accumulation value is less than the threshold value TH2. In this case, for example, the integrated control unit 71 may derive, as the second accumulation value, a value obtained by multiplying the first accumulation value received in Step 219A by the transmittance. For example, in Step 230A, the integrated control unit 71 may determine whether the first accumulation value is less than a value obtained by dividing the threshold value TH2 by the transmittance.

In a case in which the determination result in Step 230A is "No", the process proceeds to Step 232. In a case in which the determination result is "Yes", the process proceeds to Step 234.

In Step 236A, the integrated control unit 71 derives, as the second imaging conditions, the tube voltage and the tube current at which the second accumulation value is equal to or greater than the threshold value TH2 in a case in which the irradiation period and the number of imaging operations are the same as the irradiation period and the number of imaging operations in the first imaging conditions. Specifically, for example, the integrated control unit 71 multiplies a ratio, which is obtained by dividing the threshold value TH2 by the second accumulation value received in Step 219A, by the actual value of the tube current acquired in Step 234 to derive the tube current in the second imaging conditions. In this case, the integrated control unit 71 may add a predetermined margin to the derived tube current.

In a case in which the derived tube current is equal to or less than the upper limit of the tube current that can be set to the radiation source 14, the integrated control unit 71 uses the tube voltage in the second imaging conditions as the tube voltage acquired in Step 234. On the other hand, in a case in which the derived tube current is greater than the upper limit of the tube current that can be set to the radiation source 14, the integrated control unit 71 uses the tube voltage in the second imaging conditions as the upper limit of the tube current that can be set to the radiation source 14. In this case, the integrated control unit 71 derives a tube voltage, which is obtained by increasing the tube voltage acquired in Step 234 by a value that corresponds to the amount of radiation corresponding to the difference between the derived tube current and the upper limit of the tube current, as the tube voltage in the second imaging conditions.

As described above, according to this embodiment, it is possible to obtain the same effect as that in the first embodiment.

In addition, according to this embodiment, the amount of radiation emitted to the second radiation detector is sequentially detected. According to this embodiment, in a case in which the accumulation value of the detected dose is less than the threshold value, the tube voltage and the tube current at which the accumulation value is equal to or greater than the threshold value in a case in which the number of imaging operations is equal to that in the first imaging conditions are derived as the second imaging conditions. Therefore, it is possible to determine whether the amount of radiation emitted to the second radiation detector is less than the threshold value earlier than in the first embodiment.

In this embodiment, the case in which the pixels 32E are provided on the TFT substrate 30B and the amount of radiation emitted to the second radiation detector 20B is sequentially detected has been described. However, the invention is not limited thereto. For example, the amount of radiation emitted to the second radiation detector 20B may be sequentially detected by a sensor that is provided separately from the second radiation detector 20B. In this case, for example, a sensor that detects the amount of radiation R is provided in a region that is irradiated with the radiation R between the radiation limitation member 24 and the second radiation detector 20B.

In the second imaging process (see FIG. 17), in a case in which the second accumulation value derived in Step 193 is equal to or greater than the threshold value TH2, the process after Step 195 may be performed even before the irradiation period elapses. In this case, for example, the control unit 58B may transmit command information indicating a command to stop the emission of the radiation R to the radiation emitting apparatus 12 through the console 18.

Third Embodiment

Next, a third embodiment of the invention will be described in detail. Since a radiography system 10 according to this embodiment has the same structure as the radiography system according to the first embodiment (see FIGS. 1 to 4), the description thereof will not be repeated here. In addition, components having the same functions as those in the first embodiment are denoted by the same reference numerals and the description thereof will not be repeated. Hereinafter, the imaging operation for obtaining an ES image and bone density which has been performed in the first embodiment and the second embodiment is referred to as a "main imaging operation".

In this embodiment, for example, a case in which a preliminary imaging operation in which the amount of radiation emitted is less than that in the main imaging operation is performed prior to the main imaging operation in order to align the position of the subject W will be described. That is, in the preliminary imaging operation, at least one of the value of the tube voltage, the value of the tube current, or the value of the irradiation period of the emission conditions included in the first imaging conditions is less than those in the main imaging operation and thus a radiographic image is captured in a state in which the amount of radiation is less than that in the main imaging operation.

In this embodiment, a case in which the imaging conditions (that is, second imaging conditions) of the main imaging operation are derived, using the first radiographic image data captured by the first radiation detector 20A of the radiation detectors 20, in the preliminary imaging operation will be described.

Next, the operation of the radiography system 10 according to this embodiment will be described with reference to FIGS. 19 to 23. Since the process flow of an image generation processing program and a first imaging processing program according to this embodiment is the same as that in the first embodiment (see FIGS. 7 and 12), the description thereof will not be repeated here.

Figure 19:
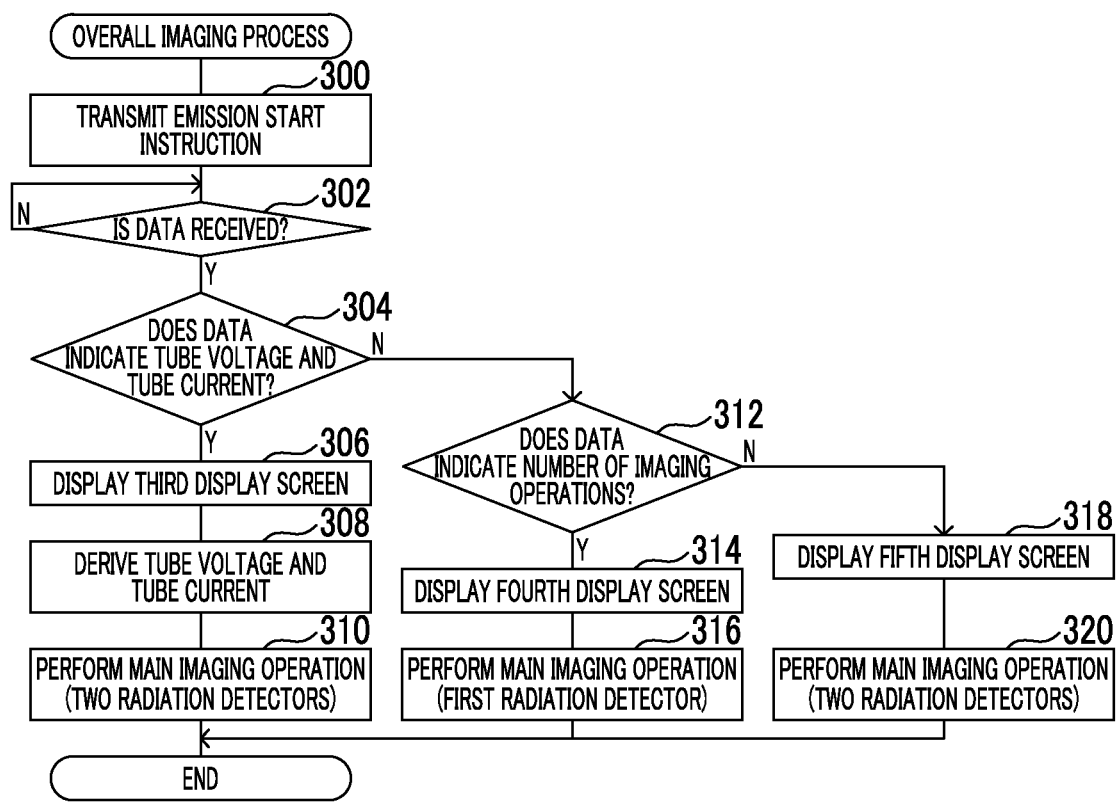
FIG. 19 is a flowchart illustrating the process flow of an overall imaging processing program according to the third embodiment.

FIG. 19 is a flowchart illustrating the process flow of an overall imaging processing program which is executed by the CPU 80 of the console 18 in a case in which the user inputs an imaging menu including, for example, the name of the subject W, an imaging part, and the first imaging conditions through the operation panel 90. The overall imaging processing program is installed in the ROM 82 of the console 18 in advance.

Figure 22:
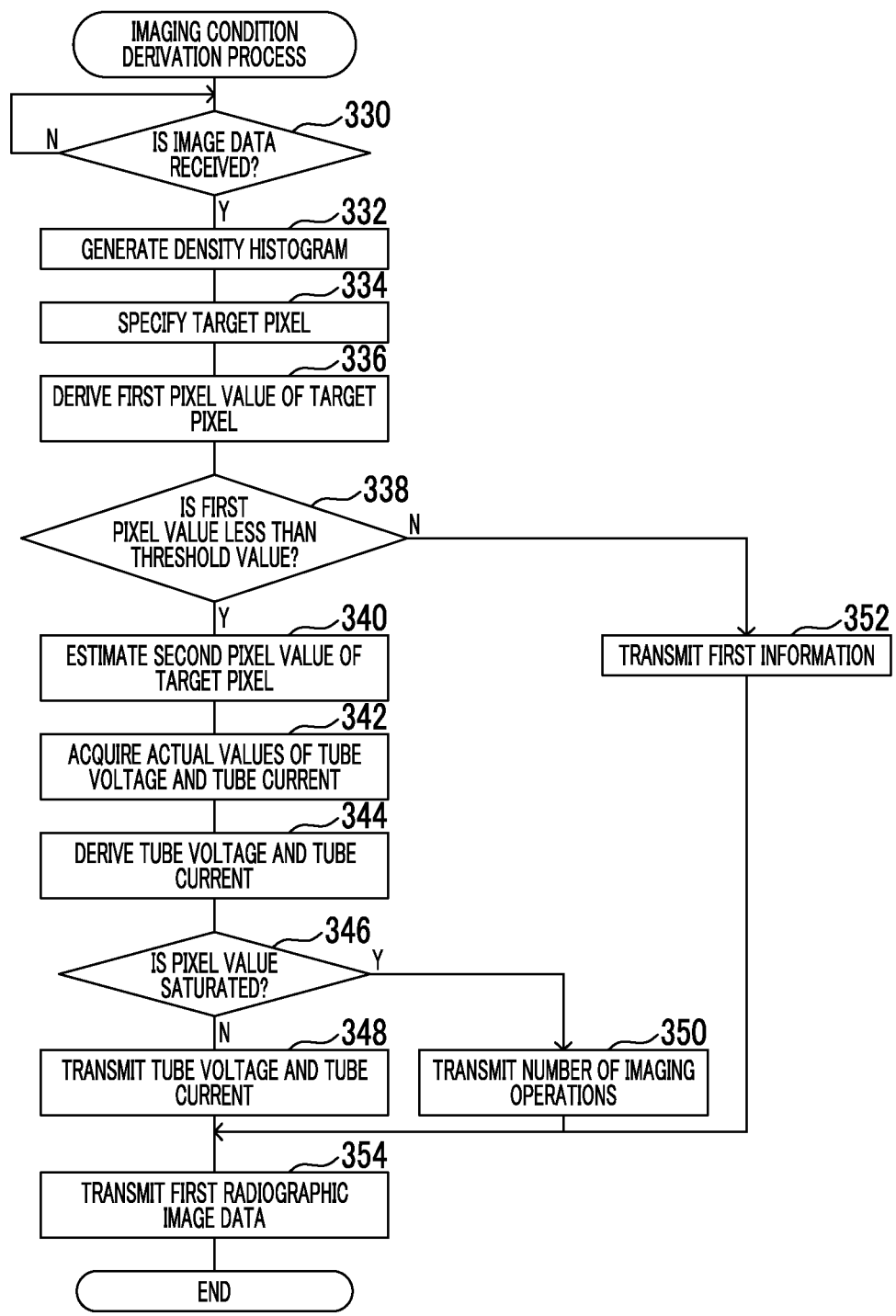
FIG. 22 is a flowchart illustrating the process flow of an imaging condition derivation processing program according to the third embodiment.

FIG. 22 is a flowchart illustrating the process flow of an imaging condition derivation processing program that is executed by the integrated control unit 71 of the radiography apparatus 16 in a case in which the radiography apparatus 16 is in an on state. The imaging condition derivation processing program is installed in the ROM of the memory 74 of the integrated control unit 71 in advance.

In Step 300 of FIG. 19, similarly to Step 100, the CPU 80 transmits information included in the input imaging menu to the radiography apparatus 16 through the communication unit 92 and transmits the emission conditions of the radiation R to the radiation emitting apparatus 12 through the communication unit 92. Then, the CPU 80 transmits a command to start the emission of the radiation R to the radiography apparatus 16 and the radiation emitting apparatus 12 through the communication unit 92. When receiving the emission conditions and the emission start command transmitted from the console 18, the radiation emitting apparatus 12 starts the emission of the radiation R according to the received emission conditions.

Then, in Step 302, the CPU 80 waits until the first radiographic image data, information indicating the tube voltage and the tube current, imaging number information, or first information which will be described below is received. When the CPU 80 receives the first radiographic image data transmitted by the radiography apparatus 16 and receives the information indicating the tube voltage and the tube current, the imaging number information, or the first information, the determination result in Step 302 is "Yes" and the process proceeds to Step 304.

In Step 304, the CPU 80 determines whether the data received in Step 302 includes the information indicating the tube voltage and the tube current transmitted in Step 348 of an imaging condition derivation process which will be described below. In a case in which the determination result is "Yes", the process proceeds to Step 306.

Figure 20:
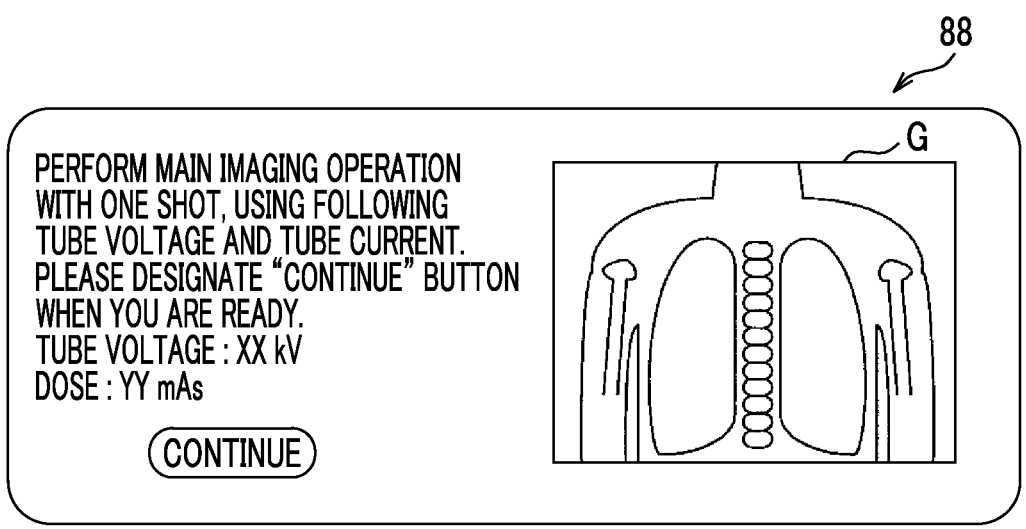
FIG. 20 is a diagram schematically illustrating an example of a third display screen according to the third embodiment.

In Step 306, the CPU 80 displays a third display screen, on which the information indicating the tube voltage and the tube current received in Step 302 and the first radiographic image indicated by the first radiographic image data are displayed, on the display unit 88. FIG. 20 illustrates an example of the third display screen. As illustrated in FIG. 20, the same information as that displayed on the first display screen and a first radiographic image G indicated by the first radiographic image data received in Step 302 are displayed on the third display screen according to this embodiment.

The user visually checks the first radiographic image G and aligns the position of the subject W, if necessary. In a case in which the user continues to capture a radiographic image, the user designates a "continue" button displayed in the lower part of the third display screen. When the "continue" button is designated, the process proceeds to Step 308.

In Step 308, similarly to Step 112, the CPU 80 derives the set values of the tube voltage and the tube current in the second imaging conditions. Then, in Step 310, similarly to Step 114, the CPU 80 performs control for the main imaging operation, using the tube voltage and the tube current derived in Step 308, and then ends the overall imaging process.

In a case in which the determination result in Step 304 is "No", the process proceeds to Step 312. In Step 312, the CPU 80 determines whether the data received in Step 302 includes the imaging number information transmitted in Step 350 of the imaging condition derivation process which will be described below. In a case in which the determination result is "Yes", the process proceeds to Step 314.

Figure 21:
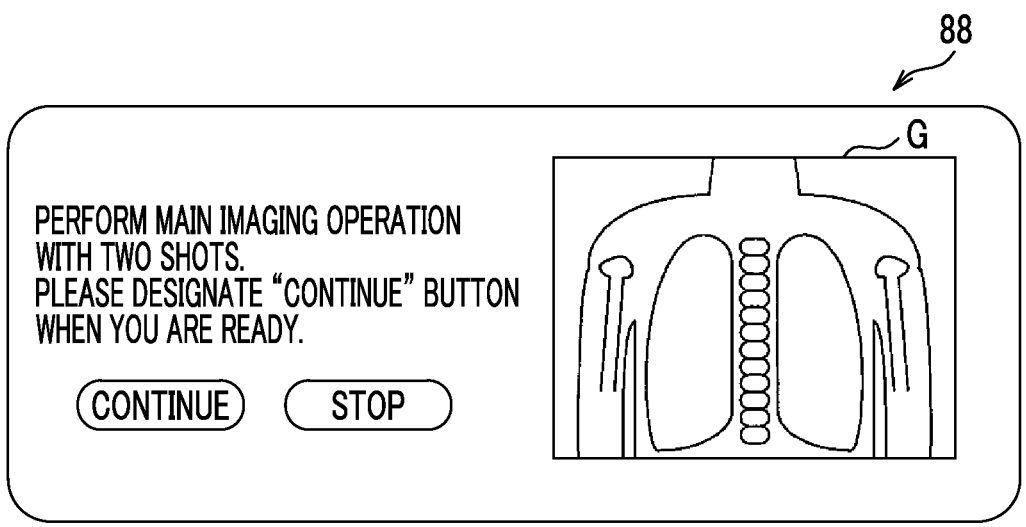
FIG. 21 is a diagram schematically illustrating an example of a fourth display screen according to the third embodiment.

In Step 314, the CPU 80 displays a fourth display screen, on which the imaging number information received in Step 302 and the first radiographic image indicated by the first radiographic image data are displayed, on the display unit 88. FIG. 21 illustrates an example of the fourth display screen. As illustrated in FIG. 21, the same information as that displayed on the second display screen and a first radiographic image G indicated by the first radiographic image data received in Step 302 are displayed on the fourth display screen according to this embodiment. The user visually checks the first radiographic image G and aligns the position of the subject W, if necessary. In a case in which the user continues to capture a radiographic image, the user designates a "continue" button displayed in the lower part of the fourth display screen. When the "continue" button is designated, the process proceeds to Step 316. In contrast, in a case in which the user stops the capture of a radiographic image, the user designates a "stop" button displayed in the lower part of the fourth display screen. When the "stop" button is designated, the CPU 80 stops the execution of the overall imaging processing program and changes the radiography apparatus 16 to a standby state.

In Step 316, the CPU 80 performs control for the main imaging operation, using conditions that are predetermined as the emission conditions of the main imaging operation, as in Step 120, and ends the overall imaging process.

On the other hand, in a case in which the determination result in Step 312 is "No", it is considered that the data received in Step 302 includes the first information transmitted in Step 352 of the imaging condition derivation process which will be described below and the process proceeds to Step 318.

In Step 318, the CPU 80 displays a fifth display screen, on which information indicating the tube voltage and the tube current that are predetermined as the emission conditions in the main imaging operation and the first radiographic image indicated by the first radiographic image data are displayed, on the display unit 88. Since the fifth display screen differs from the third display screen only in that the values of the tube voltage and the tube current are displayed, the description thereof will not be repeated here.

In Step 320, the CPU 80 performs control for the main imaging operation, using the predetermined conditions, as in Step 114 and then ends the overall imaging process.

In Step 330 of FIG. 22, the integrated control unit 71 waits until the first radiographic image data is received. When the integrated control unit 71 receives the first radiographic image data transmitted in Step 180 of the first imaging process, the determination result in Step 330 is "Yes" and the process proceeds to Step 332.

Figure 23:
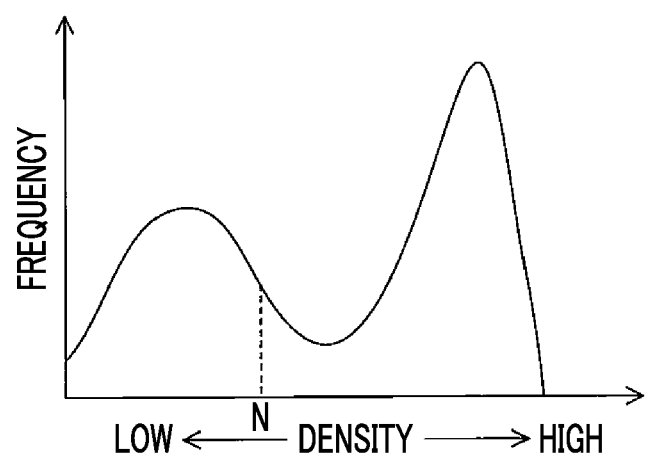
FIG. 23 is a graph illustrating an example of a density histogram.

In Step 332, the integrated control unit 71 generates a density histogram, using the first radiographic image data received in Step 330. FIG. 23 illustrates an example of the density histogram. FIG. 23 illustrates the density histogram in a case in which an image of the chest of the subject W is captured. In FIG. 23, a peak at the right end corresponds to the density of the pixels in an unexposed portion irradiated with radiation that is not transmitted through the subject W. Then, the integrated control unit 71 specifies density N which is a relatively low value in a region of the first radiographic image in which radiation is transmitted through the subject W, on the basis of the generated density histogram and the imaging part. For example, in the example illustrated in FIG. 23, the integrated control unit 71 specifies the density N of the pixels corresponding to the mediastinum of the subject W.

Then, in Step 334, the integrated control unit 71 specifies pixels which have a density less than the density N specified in Step 332 in the first radiographic image data received in Step 330 as pixels to be processed (hereinafter, referred to as "processing target pixels"). Then, in Step 336, the integrated control unit 71 derives, as the first pixel value, the average value of the pixel values of the processing target pixels in the first radiographic image data. The average value of the pixel values of a region in which the amount of radiation is relative small in the region of interest is derived by the process from Step 332 to Step 336.

In Step 338, the integrated control unit 71 determines whether the first pixel value derived in Step 336 is less than a predetermined threshold value TH3. For example, a value that is obtained as the lower limit at which the quality of the ES image and the accuracy of bone density obtained in Step 106 of the main imaging operation are within the allowable range by experiments using the actual radiography apparatus 16 may be applied as the threshold value TH3. In a case in which the determination result in Step 338 is "Yes", the process proceeds to Step 340.

In Step 340, the integrated control unit 71 derives a value obtained by multiplying the first pixel value derived in Step 334 by the transmittance as the estimated value of the second pixel value. Then, in Step 342, the integrated control unit 71 acquires the actual values of the tube voltage and the tube current of the radiation source 14 in the current preliminary imaging operation from the radiation source 14 through the console 18. Then, in Step 344, similarly to Step 236, the integrated control unit 71 derives the tube voltage and the tube current at which the second pixel value is equal to or greater than the threshold value TH1 in the main imaging operation, using the second pixel value derived in Step 340.

Then, in Step 346, similarly to Step 238, in a case in which the tube voltage and the tube current derived in Step 344 are set to the radiation source 14 and radiographic images are captured, the integrated control unit 71 determines whether the pixel value of the first radiographic image data is saturated. In a case in which the determination result is "Yes", the process proceeds to Step 350. In a case in which the determination result is "No", the process proceeds to Step 348.

In Step 348, the integrated control unit 71 transmits information indicating the tube voltage and the tube current derived in Step 344 to the console 18 through the communication unit 66. In Step 350, the integrated control unit 71 transmits imaging number information indicating that a plurality of imaging operations (two imaging operations in this embodiment) are performed to the console 18 through the communication unit 66.

On the other hand, in a case in which the determination result in Step 338 is "No", the process proceeds to Step 352. In Step 352, the integrated control unit 71 transmits first information indicating that the first pixel value derived in Step 336 is equal to or greater than the threshold value TH3 to the console 18 through the communication unit 66.

In Step 354, the integrated control unit 71 transmits the first radiographic image data received in Step 330 to the console 18 through the communication unit 66 and then ends the imaging condition derivation process. When data is transmitted in Step 348, Step 350, or Step 352 and Step 354, the determination result in Step 302 of the overall imaging process is "Yes".

During the preliminary imaging operation, the second imaging process or a process of sweeping the charge accumulated in the pixels 32 may be performed for the second radiation detector 20B.

As described above, according to this embodiment, it is possible to obtain the same effect as that in the first embodiment.

According to this embodiment, the second imaging conditions are derived on the basis of the first radiographic image data in the preliminary imaging operation. Therefore, it is possible to derive the second imaging conditions with a smaller amount of radiation than that in the first and second embodiments.

Fourth Embodiment

Next, a fourth embodiment of the invention will be described in detail. Since a radiography system 10 according to this embodiment has the same structure as the radiography system according to the first embodiment (see FIGS. 1 to 4), the description thereof will not be repeated here. In addition, components having the same functions as those in the first embodiment are denoted by the same reference numerals and the description thereof will not be repeated.

The operation of the radiography system 10 according to this embodiment will be described with reference to FIGS. 24 to 26. Since the process flow of an image generation processing program, a first imaging processing program, and a second imaging processing program according to this embodiment is the same as that in the first embodiment (see FIG. 7, FIG. 12, and FIG. 13), the description thereof will not be repeated here.

Figure 24:
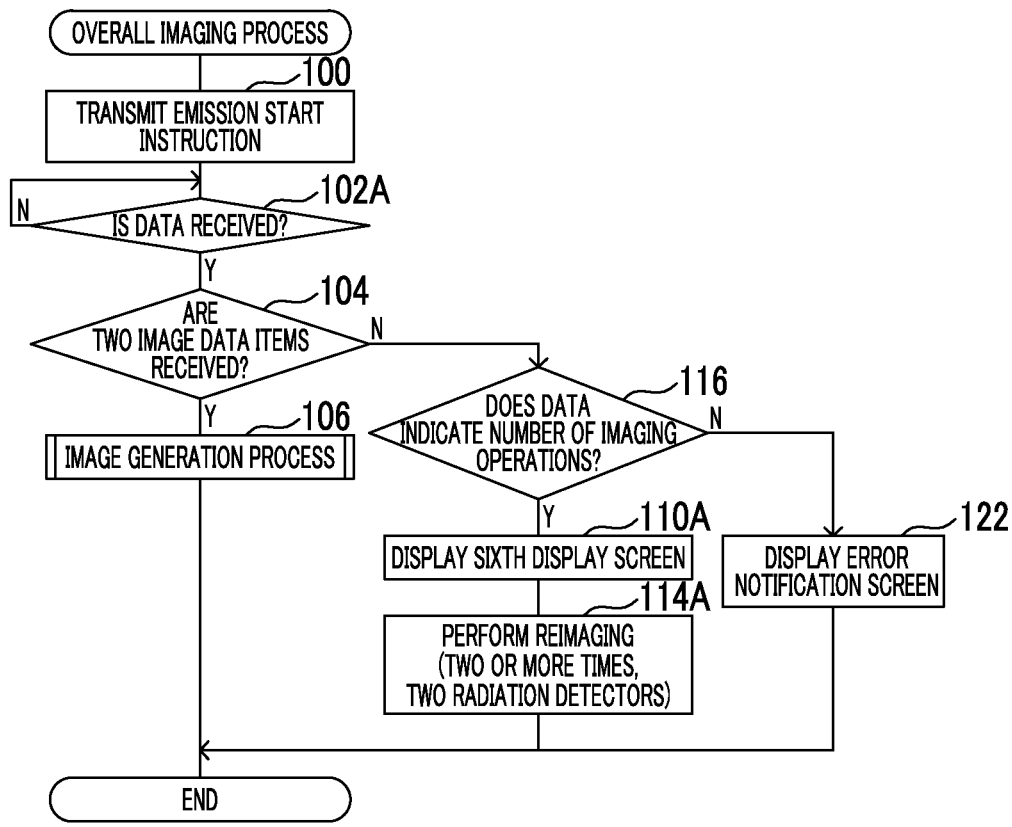
FIG. 24 is a flowchart illustrating the process flow of an overall imaging processing program according to the fourth embodiment.
Figure 25:
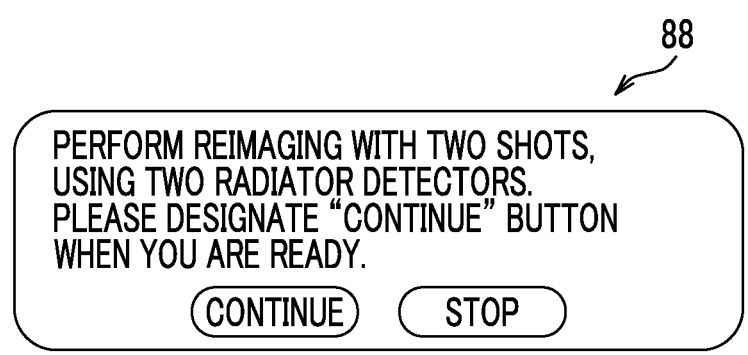
FIG. 25 is a diagram schematically illustrating an example of a sixth display screen according to the fourth embodiment.

FIG. 24 is a flowchart illustrating the process flow of an overall imaging processing program which is executed by the CPU 80 of the console 18 in a case in which the user inputs an imaging menu including, for example, the name of the subject W, an imaging part, and the first imaging conditions through the operation panel 90. The overall imaging processing program is installed in the ROM 82 of the console 18 in advance. In FIG. 24, steps in which the same processes as those in FIG. 6 are performed are denoted by the same step numbers as those in FIG. 6 and the description thereof will not be repeated.

Figure 26:
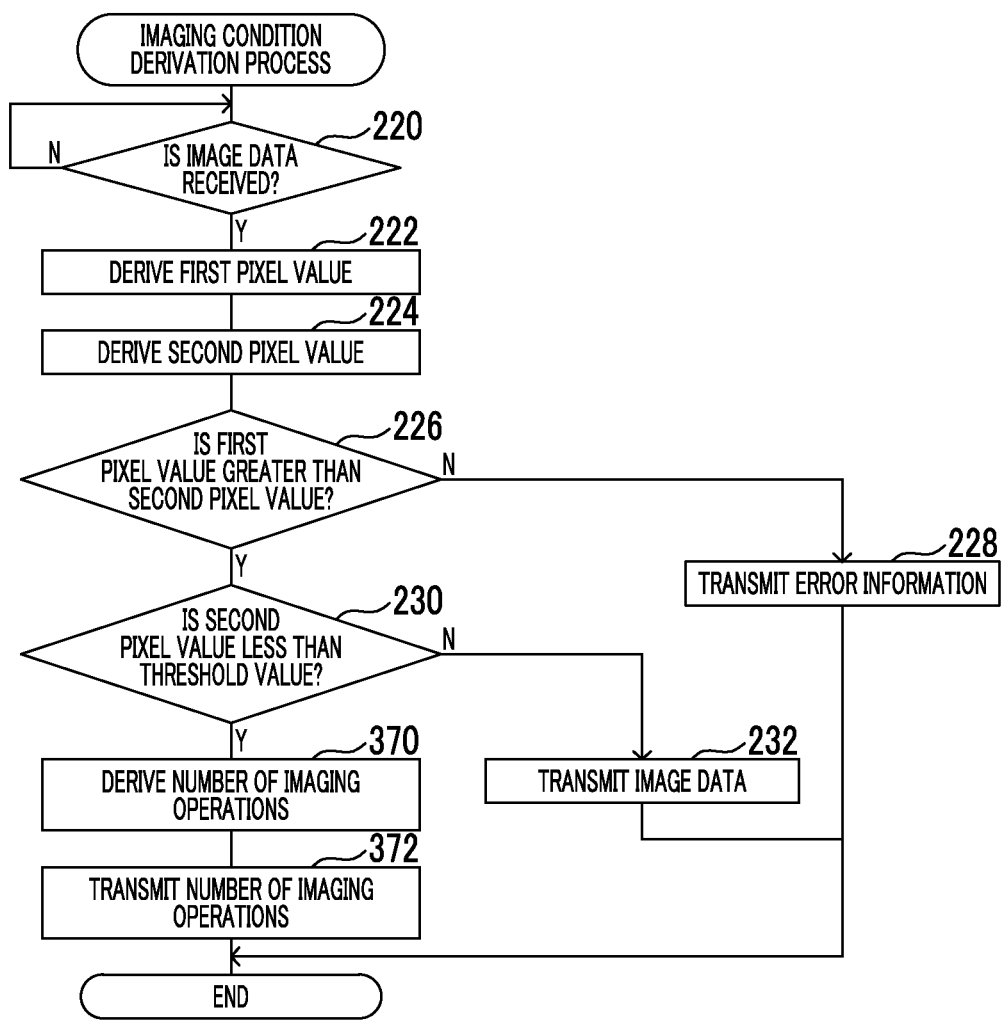
FIG. 26 is a flowchart illustrating the process flow of an imaging condition derivation processing program according to the fourth embodiment.

FIG. 26 is a flowchart illustrating the process flow of an imaging condition derivation processing program that is executed by the integrated control unit 71 of the radiography apparatus 16 in a case in which the radiography apparatus 16 is in an on state. The imaging condition derivation processing program is installed in the ROM of the memory 74 of the integrated control unit 71 in advance. In FIG. 26, steps in which the same processes as those in FIG. 14 are performed are denoted by the same step numbers as those in FIG. 14 and the description thereof will not be repeated.

In Step 102A of FIG. 24, the CPU 80 waits until data transmitted by the radiography apparatus 16 is received. When the CPU 80 receives any one of error information, first and second radiographic image data items, and imaging number information transmitted by the radiography apparatus 16, the determination result in Step 102A is "Yes" and the process proceeds to Step 104.

In a case in which the determination result in Step 116 is "Yes", the process proceeds to Step 110A. In a case in which the determination result is "No", it is considered that the data received in Step 102A is the error information transmitted in Step 228 and the process proceeds to Step 122. When the CPU 80 receives the imaging number information transmitted in Step 372 of the imaging condition derivation process which will be described below, the determination result in Step 116 is "Yes".

In Step 110A, the CPU 80 displays a sixth display screen, on which the imaging number information received in Step 102A is displayed, on the display unit 88. FIG. 25 illustrates an example of the sixth display screen. As illustrated in FIG. 25, information indicating that the same number of reimaging operations as the number of imaging operations (in this embodiment, the number of imaging operations is two. In the example illustrated in FIG. 25, the number of imaging operations is represented by "two shots") indicated by the imaging number information received in Step 102A is performed, using two radiation detectors, is displayed on the sixth display screen according to this embodiment. In a case in which the user continues to capture a radiographic image, the user designates a "continue" button which is displayed in a lower part of the sixth display screen. When the "continue" button is designated, the process proceeds to Step 114A. In contrast, in a case in which the user stops the capture of a radiographic image, the user designates a "stop" button displayed in the lower part of the sixth display screen. When the "stop" button is designated, the CPU 80 stops the execution of the overall imaging processing program and changes the radiography apparatus 16 to a standby state.

In Step 114A, the CPU 80 performs control for reimaging and then ends the overall imaging process. Specifically, first, the CPU 80 performs control for capturing a radiographic image under the same condition as the emission condition in the first imaging conditions. Then, the CPU 80 receives the first radiographic image data captured by the first radiation detector 20A and the second radiographic image data captured by the second radiation detector 20B.

The CPU 80 repeatedly performs the above-mentioned control process the number of times corresponding to the number of imaging operations indicated by the imaging number information received in Step 102A. Then, the CPU 80 receives the same number of first radiographic image data items and second radiographic image data items as the number of imaging operations.

The CPU 80 derives the average value of the pixel values of the corresponding pixels in the received plurality of first radiographic image data items to generate first average image data. In addition, the CPU 80 derives the average value of the pixel values of the corresponding pixels in the received plurality of second radiographic image data items to generate second average image data. Then, the CPU 80 performs the image generation process, using the first average image data and the second average image data, to generate ES image data and to derive bone density.

In Step 370 of FIG. 26, the integrated control unit 71 derives a predetermined number of (this embodiment, two)

imaging operations as the number of imaging operations in the second imaging conditions. In addition, for example, the integrated control unit 71 may derive the number of imaging operations which increases as the second pixel value derived in Step 224 decreases as the number of imaging operations in the second imaging conditions.

Then, in Step 372, the integrated control unit 71 transmits imaging number information indicating the number of imaging operations derived in Step 370 to the console 18 through the communication unit 66 and ends the imaging condition derivation process.

As described above, according to this embodiment, it is possible to obtain the same effect as that in the first embodiment.

According to this embodiment, a radiographic image is captured under the second imaging conditions, without changing the set values of the tube voltage and the tube current of the radiation source 14. Therefore, it is possible to capture a radiographic image under the second imaging conditions even in a case in which a relatively inexpensive radiation source in which the set values of a tube voltage and a tube current are unchangeable is used.

In a case in which imaging is performed a plurality of times, the user may select and change the method for performing a plurality of imaging operations described in the fourth embodiment and the method for performing a plurality of imaging operations described in the first to third embodiments.

In each of the above-described embodiments, the case in which an indirect-conversion-type radiation detector that converts radiation into light and converts the converted light into charge is applied to both the first radiation detector 20A and the second radiation detector 20B has been described. However, the invention is not limited thereto. For example, a direct-conversion-type radiation detector that directly converts radiation into charge may be applied to at least one of the first radiation detector 20A or the second radiation detector 20B.

In each of the above-described embodiments, the case in which the irradiation side sampling radiation detectors in which the radiation R is incident from the TFT substrates 30A and 30B are applied to the first radiation detector 20A and the second radiation detector 20B, respectively, has been described. However, the invention is not limited thereto. For example, a so-called penetration side sampling (PSS) radiation detector in which the radiation R is incident from the scintillator 22A or 22B may be applied to at least one of the first radiation detector 20A or the second radiation detector 20B.

In each of the above-described embodiments, the functions implemented by the integrated control unit 71 may be implemented by any one of the CPU 80 of the console 18, the control unit 58A, and the control unit 58B. In addition, for example, two or more of the control unit 58A, the control unit 58B, and the integrated control unit 71 may be integrated with each other.

In each of the above-described embodiments, the case in which bone density is derived using the first radiographic image and the second radiographic image has been described. However, the invention is not limited thereto. For example, bone mineral content or both bone density and bone mineral content may be derived using the first radiographic image and the second radiographic image.

In each of the above-described embodiments, in a case in which the body thickness of the subject W is equal to or greater than a predetermined value, a plurality of imaging operations may be performed. In this case, for example, an ultrasonic distance measurement device is provided in the radiation emitting apparatus 12 and measures the distance from the radiation emitting apparatus 12 to the subject W and the distance from the radiation emitting apparatus 12 to the radiography apparatus 16. Then, the body thickness of the subject W is calculated from the difference between the two measured distances. In addition, the body thickness of the subject W is estimated from the height and weight of the subject W included in the information of the subject W.

In each of the above-described embodiments, the integrated control unit 71 may select some imaging conditions from a plurality of imaging conditions which are prepared in advance and derive the second imaging conditions.

In each of the above-described embodiments, the aspect in which the overall imaging processing program is stored (installed) in the ROM 82 in advance has been described. However, the invention is not limited thereto. The overall imaging processing program may be recorded in a recording medium, such as a compact disk read only memory (CD-ROM), a digital versatile disk read only memory (DVD-ROM), or a universal serial bus (USB) memory, and then provided. In addition, the overall imaging processing program may be downloaded from an external apparatus through a network.

In each of the above-described embodiments, the aspect in which the first imaging processing program is stored in the ROM of the memory 62 of the control unit 58A in advance and the second imaging processing program is stored in the ROM of the memory 62 of the control unit 58B in advance has been described. However, the invention is not limited thereto. The first imaging processing program and the second imaging processing program may be recorded in the above-mentioned recording medium and then provided. In addition, the first imaging processing program and the second imaging processing program may be downloaded from an external apparatus through the network.

In each of the above-described embodiments, the aspect in which the imaging condition derivation processing program is stored in the ROM of the memory 74 of the integrated control unit 71 in advance has been described. However, the invention is not limited thereto. The imaging condition derivation processing program may be recorded in the above-mentioned recording medium and then provided. In addition, the imaging condition derivation processing program may be downloaded from an external apparatus through the network.

What is claimed is:

1. A radiography system comprising:
 a radiography apparatus comprising
  a first radiation detector in which a plurality of pixels, each of which includes a conversion element that generates a larger amount of charge as it is irradiated with a larger amount of radiation, are two-dimensionally arranged, and
  a second radiation detector which is provided so as to be stacked on a side of the first radiation detector from which the radiation is transmitted and emitted and in which a plurality of pixels, each of which includes a conversion element that generates a larger amount of charge as it is irradiated with a larger amount of radiation, are two-dimensionally arranged; and
 a derivation unit that is configured to, in a case in which a value corresponding to at least one of a first electric signal or a second electric signal is less than a threshold value, automatically derive second imaging conditions using at least one of the first electric signal or the second electric signal, the first electric signal being a signal obtained by converting charge generated in the pixels of the first radiation detector when imaging is performed by the radiography apparatus under first imaging conditions, and having a level that increases as an amount of charge increases, the second electric signal being a signal obtained by converting charge generated in the pixels of the second radiation detector when imaging is performed by the radiography apparatus under the first imaging conditions, and having a level that increases as an amount of charge increases, wherein each of the first imaging conditions and the second imaging conditions include a tube voltage and an amount of radiation including a tube current, the tube voltage and the tube current being set to a radiation source that emits the radiation.

2. The radiography system according to claim 1,
wherein the first imaging conditions further include a number of imaging operations set to a radiation source that emits the radiation, and
the derivation unit is further configured to, in a case in which an amount of charge accumulated in the pixels of the second radiation detector, when imaging is performed by the radiography apparatus under the first imaging conditions, is less than the threshold value, derive, as the second imaging conditions, the tube voltage and the amount of radiation including the tube current at which the amount of charge is equal to or greater than the threshold value, in a case in which a number of imaging operations is equal to the number of imaging operations in the first imaging conditions.

3. The radiography system according to claim 1, further comprising a detection unit that is configured to detect an amount of radiation emitted to the second radiation detector,
wherein the first imaging conditions further include a number of imaging operations set to a radiation source that emits the radiation, and
the derivation unit is further configured to, in a case in which an accumulation value of the amount of radiation detected by the detection unit, when imaging is performed by the radiography apparatus under the first imaging conditions, is less than the threshold value, derive, as the second imaging conditions, the tube voltage and the amount of radiation including the tube current at which the accumulation value is equal to or greater than the threshold value, in a case in which a number of imaging operations is equal to the number of imaging operations in the first imaging conditions.

4. The radiography system according to claim 1,
wherein the tube voltage and the amount of radiation including the tube current, which are included in the first imaging conditions, are set to a radiation source that emits the radiation in a preliminary imaging operation that is performed prior to a main imaging operation and in which an amount of radiation is less than an amount of radiation in the main imaging operation, and
the derivation unit is further configured to, in a case in which the amount of charge accumulated in the pixels of the first radiation detector, when imaging is performed by the radiography apparatus under the first imaging conditions, is less than the threshold value, derive, as the second imaging conditions, the tube voltage and the amount of radiation including the tube current, at which the amount of charge accumulated in the pixels of the second radiation detector in the main imaging operation is equal to or greater than the threshold value in the main imaging operation, using the amount of charge accumulated in the pixels of the first radiation detector and a predetermined radiation transmittance of the first radiation detector.

5. The radiography system according to claim 2,
wherein the derivation unit is configured to derive, as the second imaging conditions, the tube current at which the amount of charge accumulated in the pixels of the second radiation detector is equal to or greater than the threshold value in a case in which the tube voltage is equal to the tube voltage in the first imaging conditions, and
the derivation unit is configured to, in a case in which the derived tube current is greater than an upper limit that can be set to the radiation source, set the tube current in the second imaging conditions to an upper limit and derive, as the tube voltage in the second imaging conditions, a tube voltage at which the amount of charge is equal to or greater than the threshold value.

6. The radiography system according to claim 1,
wherein the first imaging conditions further include a number of imaging operations set to a radiation source that emits the radiation, and
the derivation unit is configured to, in a case in which an amount of charge accumulated in the pixels of the second radiation detector, when imaging is performed by the radiography apparatus under the first imaging conditions, is less than the threshold value, derive, as the second imaging conditions, imaging conditions in which the tube voltage and the amount of radiation including the tube current are equal to the tube voltage and the amount of radiation including the tube current in the first imaging conditions, and the number of imaging operations is larger than the number of imaging operations in the first imaging conditions.

7. The radiography system according to claim 1, further comprising
an execution unit that is configured to perform radiographic imaging under the second imaging conditions derived by the derivation unit.

8. The radiography system according to claim 1, further comprising
a display unit that is configured to display the second imaging conditions derived by the derivation unit.

9. The radiography system according to claim 1,
wherein the derivation unit is further configured to derive an estimated value of the amount of radiation emitted to the first radiation detector in a case in which the radiation is emitted with the tube voltage and the amount of radiation including the tube current derived as the second imaging conditions, and
the derivation unit is further configured to, in a case in which the derived estimated value is greater than an upper limit, derive, as the second imaging conditions, the number of imaging operations that is larger than the number of imaging operations in the first imaging conditions again.

10. The radiography system according to claim 9,
wherein the derivation unit is further configured to derive a tube voltage that is higher than the tube voltage in a first imaging operation as a tube voltage in the second and subsequent imaging operations in the second imaging conditions.

11. The radiography system according to claim 1,
wherein each of the first radiation detector and the second radiation detector comprises a light emitting layer that is irradiated with radiation and emits light, the plurality of pixels of each of the first radiation detector and the second radiation detector generate and accumulate the charge as a result of receiving the light, and the light emitting layer of the first radiation detector and the light emitting layer of the second radiation detector have different compositions.

12. The radiography system according to claim 11, wherein the light emitting layer of the first radiation detector includes CsI, and the light emitting layer of the second radiation detector includes GOS.

13. The radiography system according to claim 1, wherein the derivation unit is configured to derive at least one of bone mineral content or bone density, using a first radiographic image captured by the first radiation detector and a second radiographic image captured by the second radiation detector according to the second imaging conditions.

14. A radiography method that is performed by a radiography apparatus comprising a first radiation detector in which a plurality of pixels, each of which includes a conversion element that generates a larger amount of charge as it is irradiated with a larger amount of radiation, are two-dimensionally arranged and a second radiation detector which is provided so as to be stacked on a side of the first radiation detector from which the radiation is transmitted and emitted and in which a plurality of pixels, each of which includes a conversion element that generates a larger amount of charge as it is irradiated with a larger amount of radiation, are two-dimensionally arranged, the method comprising:

in a case in which a value corresponding to at least one of a first electric signal or a second electric signal is less than a threshold value, automatically deriving second imaging conditions using at least one of the first electric signal or the second electric signal, the first electric signal being a signal obtained by converting charge generated in the pixels of the first radiation detector when imaging is performed by the radiography apparatus under first imaging conditions, and having a level that increases as an amount of charge increases, the second electric signal being a signal obtained by converting charge generated in the pixels of the second radiation detector when imaging is performed by the radiography apparatus under the first imaging conditions, and having a level that increases as an amount of charge increases, wherein each of the first imaging conditions and the second imaging conditions include a tube voltage and an amount of radiation including a tube current, the tube voltage and the tube current being set to a radiation source that emits the radiation.

15. A non-transitory storage medium storing a radiography program that causes a computer to execute a control processing of a radiography apparatus comprising a first radiation detector in which a plurality of pixels, each of which includes a conversion element that generates a larger amount of charge as it is irradiated with a larger amount of radiation, are two-dimensionally arranged and a second radiation detector which is provided so as to be stacked on a side of the first radiation detector from which the radiation is transmitted and emitted and in which a plurality of pixels, each of which includes a conversion element that generates a larger amount of charge as it is irradiated with a larger amount of radiation, are two-dimensionally arranged, the control processing comprising:

in a case in which a value corresponding to at least one of a first electric signal or a second electric signal is less than a threshold value, automatically deriving second imaging conditions using at least one of the first electric signal or the second electric signal, the first electric being a signal obtained by converting charge generated in the pixels of the first radiation detector when imaging is performed by the radiography apparatus under first imaging conditions, and having a level that increases as an amount of charge increases, and the second electric signal being a signal obtained by converting charge generated in the pixels of the second radiation detector when imaging is performed by the radiography apparatus under the first imaging conditions, and having a level that increases as an amount of charge increases, wherein each of the first imaging conditions and the second imaging conditions include a tube voltage and an amount of radiation including a tube current, the tube voltage and the tube current being set to a radiation source that emits the radiation.

* * * * *